(12) United States Patent  (10) Patent No.: US 8,426,405 B2
Deadman et al. (45) Date of Patent: Apr. 23, 2013

(54) THIAZOPYRIMIDINONES AND USES THEREOF

(75) Inventors: John Joseph Deadman, Carlton (AU);
Eric Dale Jones, Bentleigh East (AU);
Giang Thanh Le, Lower Templestowe (AU); David Ian Rhodes, Heidelberg Heights (AU); Neeranat Thienthong, Malvern (AU); Nicholas Andrew Vandegraaff, Prahran (AU); Lisa Jane Winfield, St. Kilda (AU)

(73) Assignee: Avexa Limited, Richmond (Victoria) (AU)

( * ) Notice: Subject to any disclaimer, the term of this patent is extended or adjusted under 35 U.S.C. 154(b) by 33 days.

(21) Appl. No.: 12/733,994

(22) PCT Filed: Jul. 2, 2009

(86) PCT No.: PCT/AU2009/000856
§ 371 (c)(1),
(2), (4) Date: Nov. 9, 2010

(87) PCT Pub. No.: WO2010/000030
PCT Pub. Date: Jan. 7, 2010

(65) Prior Publication Data
US 2011/0281861 A1 Nov. 17, 2011

Related U.S. Application Data

(60) Provisional application No. 61/161,931, filed on Mar. 20, 2009.

(30) Foreign Application Priority Data

Jul. 2, 2008 (AU) ................................ 2008903405

(51) Int. Cl.
*A61K 31/535* (2006.01)
*C07D 413/14* (2006.01)

(52) U.S. Cl.
USPC ........................................ 514/234.5; 544/117

(58) Field of Classification Search .................. 544/117; 514/234.5
See application file for complete search history.

(56) References Cited

U.S. PATENT DOCUMENTS 4,551,457 A * 11/1985 Doria et al. ................ 514/259.2

OTHER PUBLICATIONS

Huff, Joel R., "HIV Protease: A Novel Chemotherapeutic Target for AIDS," Journal of Medicinal Chemistry, vol. 34, No. 8, Aug. 1991, pp. 2305-2314.*

* cited by examiner

*Primary Examiner* — Rebecca Anderson
(74) *Attorney, Agent, or Firm* — Fish & Richardson P.C.

(57) ABSTRACT

Compounds of formula (I) or a pharmaceutically acceptable derivative, salt or prodrug thereof are disclosed. Also disclosed are methods of treating a viral infection in a subject by administering to the subject an effective amount of a compound of formula (I) or a pharmaceutically acceptable derivative, salt or prodrug thereof. Pharmaceutical compositions comprising a compound of formula (I) are also provided.

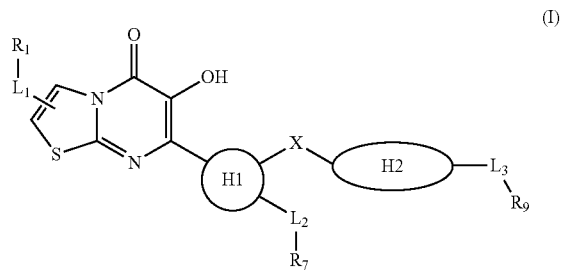

14 Claims, No Drawings

THIAZOPYRIMIDINONES AND USES THEREOF

CROSS REFERENCE TO PRIOR APPLICATIONS

This is a U.S. National Phase application under 35 U.S.C. §371 of International Patent Application No. PCT/AU2009/000856, filed Jul. 2, 2009, and claims the priority of Australian Patent Application No. 2008903405, filed Jul. 2, 2008 and U.S. Provisional Application No. 61/161,931, filed Mar. 20, 2009 all of which are incorporated by reference herein. The International Application published in English on Jan. 7, 2010 as WO 2010/000030 under PCT Article 21(2).

FIELD OF THE INVENTION

The present invention relates to a class of compounds useful in the treatment of viral infections, particularly HIV infections which show resistance to known HIV inhibitors.

BACKGROUND OF THE INVENTION

The retrovirus designated "human immunodeficiency virus" or "HIV" is the etiological agent of a complex disease that progressively destroys the immune system. This disease is known as acquired immune deficiency syndrome or AIDS. As at December 2005 an estimated 40 million people are living with HIV world wide and over 3 million deaths are occurring annually.

A feature of retrovirus replication includes the reverse transcription of the viral genome into proviral DNA and its integration into the host cell genome. These steps are required for HIV replication and are mediated by the virus encoded enzymes, reverse transcriptase and integrase respectively.

HIV infection follows a path of the virus particle binding to cell surface receptors and co-receptors resulting in fusion of the virus particle with the cell. The contents of the virus are released into the cytoplasm where reverse transcription of the HIV genome occurs. Through a series of steps a double stranded proviral DNA copy is produced. The proviral DNA is transported to the nucleus in a complex known as the pre integration complex (PIC) which contains integrase and other viral and possibly cellular proteins. Once inside the nucleus the proviral DNA is integrated into the host cell genome via the action of integrase. Once integrated, transcription and translation of the viral genome can occur resulting in the production of viral proteins and a new viral RNA genome. These proteins and genome assemble at the cell surface and, depending on cell type, possibly other intracellular membranous compartments. Assembled particles then bud out from the cell and during, or soon after, this process mature into infectious HIV particles through the action of the viral protease.

The integration of the proviral genome into the host cell genome requires the action of an integrase which carries out this process in at least three steps, possibly four. The first step involves the assembly of the viral genome into a stable nucleoprotein complex, secondly, processing of two nucleotides from the 3' termini of the genome to give staggered ends with free 3' OH residues and thirdly the transfer of these ends into the host cell genome. The final step involves the gap filling and repair of the insertion site in the host genome. There is still some conjecture over whether the integrase performs this final step or whether it is carried out by cellular repair enzymes.

Currently HIV infection can be treated with a number of inhibitors on the market which target reverse transcriptase, protease or entry into the cell. Treatment of HIV infection with these, or a combination of these, drugs is known to be an effective treatment for AIDS and similar diseases. Shortcomings with the current inhibitors include the rapid emergence and increase incidence of resistance and numerous side effects.

Certain mutations within the wild-type viral integrase enzyme are known to confer resistance to a number of known integration inhibitors published in the literature. In particular, the viral variants containing Q148H/G140S double mutation in integrase and the N155H/E92Q double mutation in integrase represent the two of the more common viruses identified that are failing treatment with Isentress (Raltegravir, MK-0518). The triple mutant Q148K/G140A/E138A is also resistant to Raltegravir. See: Kobayashi et al, Antiviral Research, received 17 Apr. 2008, accepted 17 Jun. 2008; and Vacca et al; Discovery of MK-2048-subtle changes confer unique resistance properties to a series of tricyclic hydroxypyrrole integrase strand transfer inhibitors; Abstract from the 4th IAS Conference on HIV Pathogenesis Treatment and Prevention; 22-25 Jul. 2007, Sydney, Australia.

The specifications of Australian Provisional Patent Application Nos. 2006907283, 2007902479, 2007903401 and 2007904114 and International Patent Application No PCT/AU2007/001980 which derives priority from these applications describe a broad class of compounds that inhibit HIV integrase activity. The present inventors have now determined that a sub-class of these compounds are surprisingly effective (when compared to other members of the class) against viral variants containing the Q148H/G140S double mutation in integrase and the N155H/E92Q double mutation in integrase.

SUMMARY OF THE INVENTION

In a first aspect, the present invention provides a compound of Formula I or a pharmaceutically acceptable derivative, salt or prodrug thereof wherein:

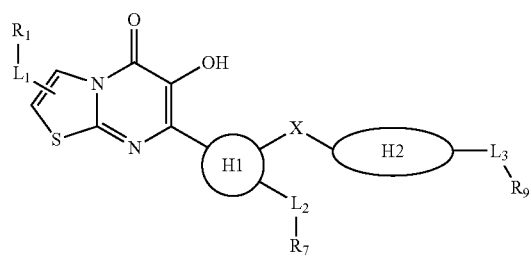

$L_1$-$R_1$ is 0-2 substituents wherein:
each $L_1$ is independently absent or is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, NH;
each $R_1$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, S(O)$N_3R_4$, $SO_2NR_3R_4$, $SO_2C_{1-10}$alkyl, and $C_{5-10}$cycloalkyl wherein one or more of the carbon atoms of the cycloalkyl ring are replaced with one or more oxygen atoms;
$R_3$ and $R_4$ are each independently selected from the group consisting of hydrogen, $C_{1-10}$alkyl, $C_{1-10}NR_5R_6$, —(CO)(CO)NR$_5$R$_6$; or R$_3$ and R$_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, C$_{1-4}$alkyl, CO$_2$C$_{1-4}$alkyl, NR$_5$R$_6$; C$_{1-4}$alkylNR$_5$R$_6$;

R$_5$ and R$_6$ are each independently selected from the group consisting of H and C$_{1-4}$alkyl or R$_5$ and R$_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and C$_{1-4}$alkyl;

when R$_1$ is alkylaryl, the aryl group of said alkylaryl substituent is optionally substituted with a substituent selected from C$_{1-10}$alkyl, —O—C$_{1-10}$alkyl, C$_{1-10}$alkylNR$_3$R$_4$, —O—C$_{1-10}$alkylNR$_3$R$_4$, halo, NR$_3$R$_4$, alkylaryl, —O-alkylaryl, SO$_2$NR$_3$R$_4$ H$_1$ is a 5- or 6-membered saturated, partially saturated or aromatic ring containing between 1 and 4 heteroatoms wherein each heteroatom is independently selected from the group consisting of N, O and S;

L$_2$-R$_7$ is 0-2 substituents wherein:
each L$_2$ is independently absent or is group consisting of Z, C$_{1-3}$alkylene, >C=Z, —CZ$_2$—, —C(=Z)C$_{1-3}$alkylene, —CZ$_2$—C$_{1-3}$alkylene, —C$_{1-3}$alkylene-C(=Z)—, —C$_{1-3}$alkylene-CZ$_2$— wherein each Z is independently selected from O, S, and NH;

each R$_7$ is independently selected from the group consisting of hydrogen, C$_{1-10}$alkyl wherein one or more of the carbon atoms of the alkyl chain may optionally be replaced with oxygen atoms, C$_{1-10}$alkylNR$_3$R$_4$, halo, NR$_3$R$_4$, alkylaryl, S(O)N$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms;

X is CR$_8$R$_{8'}$.
each of R$_8$ and R$_{8'}$ is independently selected from the group consisting of H and CH$_3$, preferably H;

H$_2$ is a 5- or 6-membered saturated, partially saturated or aromatic ring containing between 0 and 4 heteroatoms independently selected from the group consisting of N; O and S;

L$_3$-R$_9$ is 0-3 substituents wherein:
each L$_3$ is independently absent or is selected from the group consisting of Z, C$_{1-3}$alkylene, >C=Z, —CZ$_2$—, —C(=Z)C$_{1-3}$alkylene, —CZ$_2$—C$_{1-3}$alkylene, —C$_{1-3}$alkylene-C(=Z)—, —C$_{1-3}$alkylene-CZ$_2$— wherein each Z is independently selected from O, S, and NH;

each R$_9$ is independently selected from the group consisting of hydrogen, C$_{1-10}$alkyl wherein one or more of the carbon atoms of the alkyl chain may optionally be replaced with oxygen atoms, C$_{1-10}$alkylNR$_3$R$_4$, halo, NR$_3$R$_4$, heterocyclyl, heteroaryl, alkylaryl, S(O)N$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms.

In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

In a fourth aspect, the present invention provides pharmaceutical composition comprising a compound according to the first aspect and a pharmaceutically acceptable carrier, diluent or excipient.

DETAILED DESCRIPTION OF THE INVENTION

In a first aspect, the present invention provides a compound of Formula I or a pharmaceutically acceptable derivative, salt or prodrug thereof wherein:

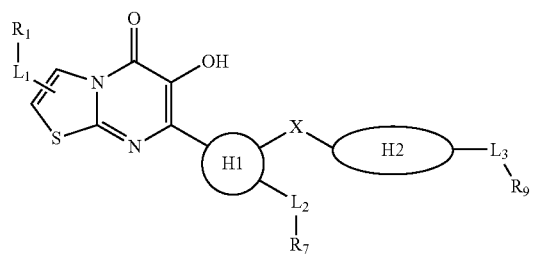

L$_1$-R$_1$ is 0-2 substituents wherein:
each L$_1$ is independently absent or is selected from the group consisting of Z, C$_{1-3}$alkylene, >C=Z, —CZ$_2$—, —C(=Z)C$_{1-3}$alkylene, —CZ$_2$—C$_{1-3}$alkylene, —C$_{1-3}$alkylene-C(=Z)—, —C$_{1-3}$alkylene-CZ$_2$— wherein each Z is independently selected from O, S, NH;

each R$_1$ is independently selected from the group consisting of hydrogen, C$_{1-10}$alkyl wherein one or more of the carbon atoms of the alkyl chain may optionally be replaced with oxygen atoms, C$_{1-10}$alkylNR$_3$R$_4$, halo, NR$_3$R$_4$, alkylaryl, S(O)N$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms;

R$_3$ and R$_4$ are each independently selected from the group consisting of hydrogen, C$_{1-10}$alkyl, C$_{1-10}$NR$_5$R$_6$, —(CO)(CO)NR$_5$R$_6$; or R$_3$ and R$_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, C$_{1-4}$alkyl, CO$_2$C$_{1-4}$alkyl, NR$_5$R$_6$; C$_{1-4}$alkylNR$_5$R$_6$;

R$_5$ and R$_6$ are each independently selected from the group consisting of H and C$_{1-4}$alkyl or R$_5$ and R$_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and C$_{1-4}$alkyl;

when R$_1$ is alkylaryl, the aryl group of said alkylaryl substituent is optionally substituted with a substituent selected from C$_{1-10}$alkyl, —O—C$_{1-10}$alkyl, C$_{1-10}$alkylNR$_3$R$_4$, —O—C$_{1-10}$alkylNR$_3$R$_4$, halo, NR$_3$R$_4$, alkylaryl, —O-alkylaryl, SO$_2$NR$_3$R$_4$ $H_1$ is a 5- or 6-membered saturated, partially saturated or aromatic ring containing between 1 and 4 heteroatoms wherein each heteroatom is independently selected from the group consisting of N, O and S;

$L_2$-$R_7$ is 0-2 substituents wherein:

each $L_2$ is independently absent or is group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;

each $R_7$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, S(O)$N_3R_4$, $SO_2NR_3R_4$, $SO_2C_{1-10}$alkyl, and $C_{5-10}$cycloalkyl wherein one or more of the carbon atoms of the cycloalkyl ring are replaced with one or more oxygen atoms;

X is $CR_8R_{8'}$, each of $R_8$ and $R_{8'}$ is independently selected from the group consisting of H and $CH_3$, preferably H;

$H_2$ is a 5- or 6-membered saturated, partially saturated or aromatic ring containing between 0 and 4 heteroatoms independently selected from the group consisting of N, O and S;

$L_3$-$R_9$ is 0-3 substituents wherein:

each $L_3$ is independently absent or is selected from the group consisting of Z, $C_{1-3}$alkylene, >C=Z, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;

each $R_9$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, heterocyclyl, heteroaryl, alkylaryl, S(O)$N_3R_4$, $SO_2NR_3R_4$, $SO_2C_{1-10}$alkyl, and $C_{5-10}$cycloalkyl wherein one or more of the carbon atoms of the cycloalkyl ring are replaced with one or more oxygen atoms.

In one embodiment, $L_1$-$R_1$ is one substituent.

Preferably, $L_1$ is —$CH_2$— and $R_1$ is N-piperidine, N-piperazine, N,N'-methyl-piperazine, or N-morpholino.

Preferably, $H_1$ is a five membered aromatic heterocycle selected from the group consisting of thiazole, oxazole, oxadiazole, imidazole, triazole, tetrazole, and thiazole. More preferably, $H_1$ is 2,5-substituted thiazole.

Preferably, $H_2$ is phenyl.

In one embodiment, $L_3$-$R_9$ is one substituent and is halo, preferably chloro or fluoro, more preferably fluoro. In another embodiment, $L_3$-$R_9$ is at least 2 substituents wherein the first $L_3$-$R_9$ is halo and in the second $L_3$-$R_9$, $L_3$ is absent or is selected from >C=O and $R_9$ is selected from the group consisting of halo, $NR_3R_4$ and $SO_2NR_3R_4$.

In one embodiment, $NR_3R_4$ where it occurs in $L_3$-$R_9$ is morpholino, a five-membered cyclic sulphonamide (such as isothiazolidine) or a six membered cyclic sulphonamide.

In another embodiment, $L_1$-$R_1$ is one substituent wherein $L_1$ is absent and $R_1$ is $C_{1-10}$alkyl, preferably methyl.

Preferably, the compound is selected from the group consisting of:

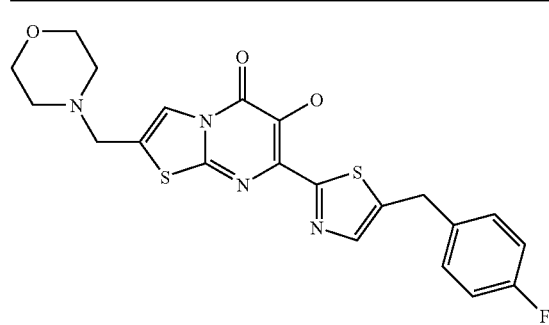

7-[5-(4-Fluoro-benzyl)-thiazol-2-yl]-6-hydroxy-2-morpholin-4-ylmethyl-thiazolo[3,2-a]pyrimidin-5-one

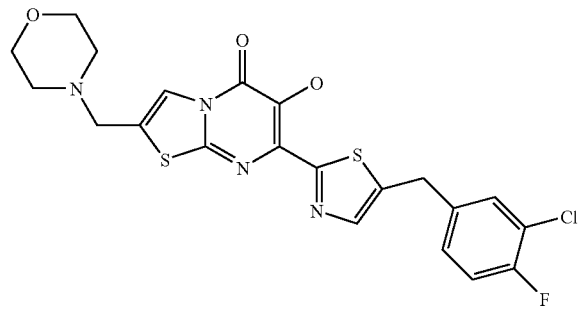 [SMILES: O=c1c(O)c(-c2ncc(Cc3ccc(F)c(Cl)c3)s2)nc2sc(CN3CCOCC3)cn12]

7-[5-(3-Chloro-4-fluoro-benzyl)-thiazol-2-yl]-6-hydroxy-2-morpholin-4-ylmethyl-thiazolo[3,2-a]pyrimidin-5-one

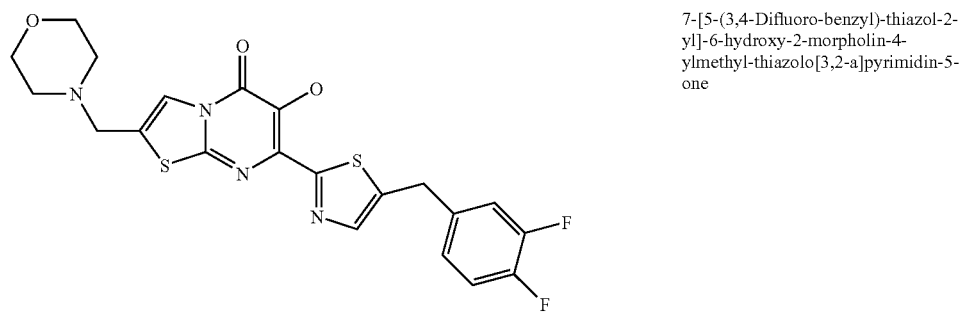

7-[5-(3,4-Difluoro-benzyl)-thiazol-2-yl]-6-hydroxy-2-morpholin-4-ylmethyl-thiazolo[3,2-a]pyrimidin-5-one

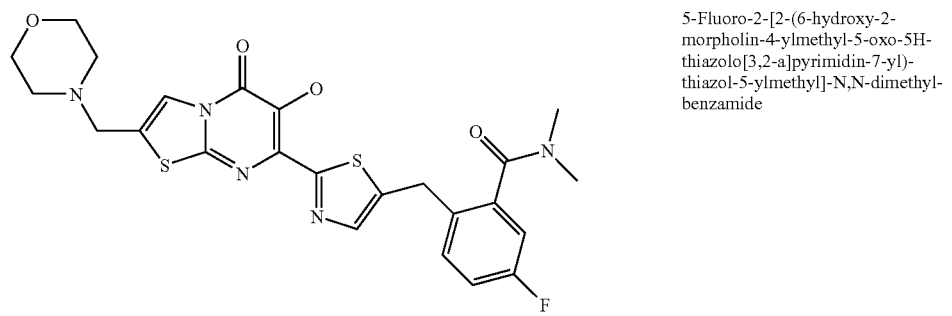

5-Fluoro-2-[2-(6-hydroxy-2-morpholin-4-ylmethyl-5-oxo-5H-thiazolo[3,2-a]pyrimidin-7-yl)-thiazol-5-ylmethyl]-N,N-dimethyl-benzamide

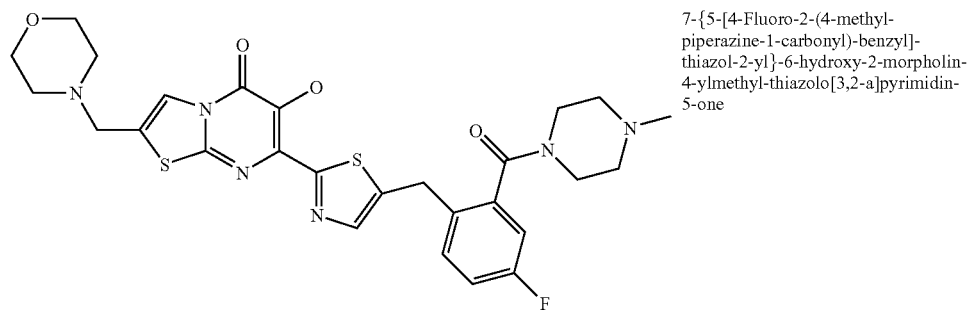

7-{5-[4-Fluoro-2-(4-methyl-piperazine-1-carbonyl)-benzyl]-thiazol-2-yl}-6-hydroxy-2-morpholin-4-ylmethyl-thiazolo[3,2-a]pyrimidin-5-one

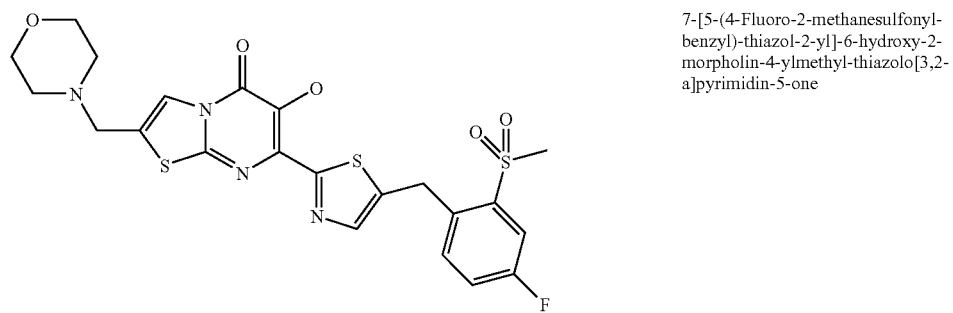

7-[5-(4-Fluoro-2-methanesulfonyl-benzyl)-thiazol-2-yl]-6-hydroxy-2-morpholin-4-ylmethyl-thiazolo[3,2-a]pyrimidin-5-one

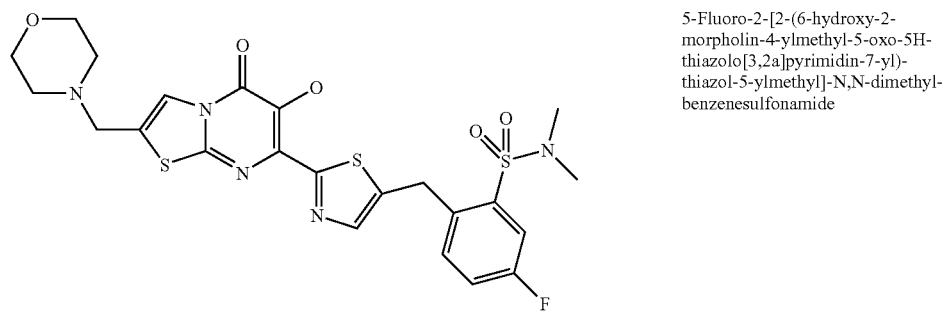

5-Fluoro-2-[2-(6-hydroxy-2-morpholin-4-ylmethyl-5-oxo-5H-thiazolo[3,2a]pyrimidin-7-yl)-thiazol-5-ylmethyl]-N,N-dimethyl-benzenesulfonamide

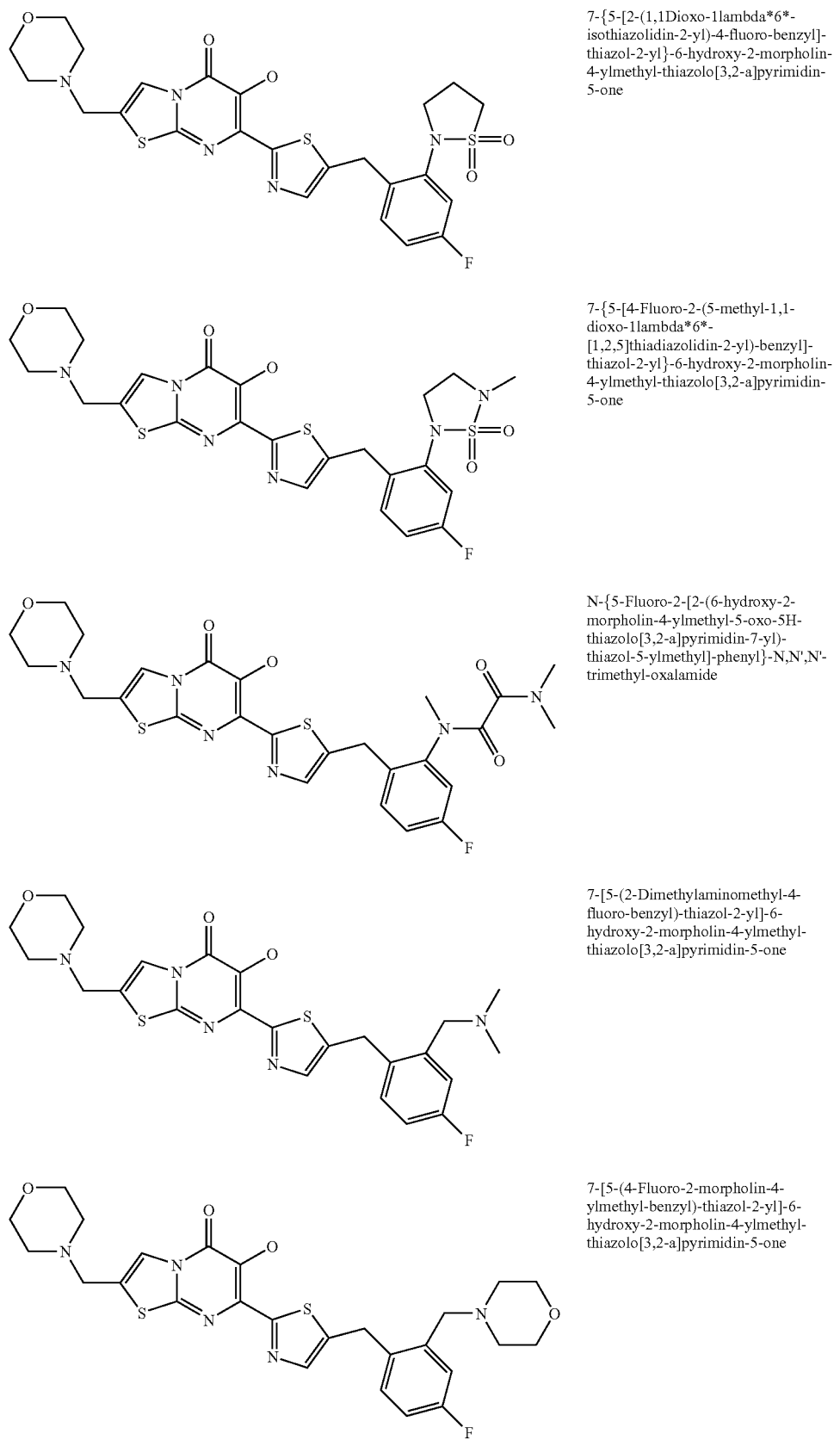

7-{5-[2-(1,1Dioxo-1lambda*6*-isothiazolidin-2-yl)-4-fluoro-benzyl]-thiazol-2-yl}-6-hydroxy-2-morpholin-4-ylmethyl-thiazolo[3,2-a]pyrimidin-5-one 7-{5-[4-Fluoro-2-(5-methyl-1,1-dioxo-1lambda*6*-[1,2,5]thiadiazolidin-2-yl)-benzyl]-thiazol-2-yl}-6-hydroxy-2-morpholin-4-ylmethyl-thiazolo[3,2-a]pyrimidin-5-one N-{5-Fluoro-2-[2-(6-hydroxy-2-morpholin-4-ylmethyl-5-oxo-5H-thiazolo[3,2-a]pyrimidin-7-yl)-thiazol-5-ylmethyl]-phenyl}-N,N',N'-trimethyl-oxalamide 7-[5-(2-Dimethylaminomethyl-4-fluoro-benzyl)-thiazol-2-yl]-6-hydroxy-2-morpholin-4-ylmethyl-thiazolo[3,2-a]pyrimidin-5-one 7-[5-(4-Fluoro-2-morpholin-4-ylmethyl-benzyl)-thiazol-2-yl]-6-hydroxy-2-morpholin-4-ylmethyl-thiazolo[3,2-a]pyrimidin-5-one

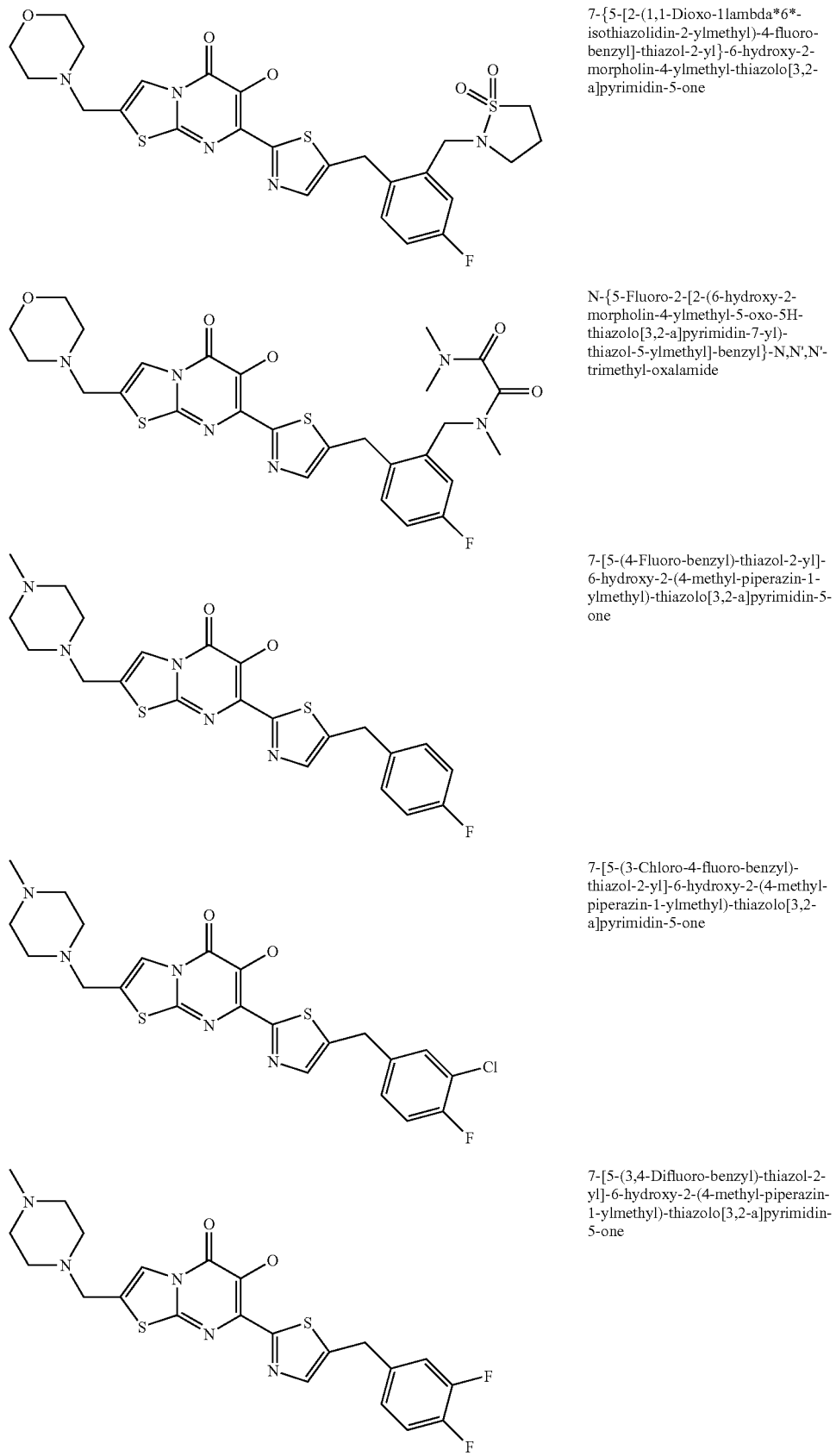

7-{5-[2-(1,1-Dioxo-1lambda*6*-isothiazolidin-2-ylmethyl)-4-fluoro-benzyl]-thiazol-2-yl}-6-hydroxy-2-morpholin-4-ylmethyl-thiazolo[3,2-a]pyrimidin-5-one N-{5-Fluoro-2-[2-(6-hydroxy-2-morpholin-4-ylmethyl-5-oxo-5H-thiazolo[3,2-a]pyrimidin-7-yl)-thiazol-5-ylmethyl]-benzyl}-N,N',N'-trimethyl-oxalamide 7-[5-(4-Fluoro-benzyl)-thiazol-2-yl]-6-hydroxy-2-(4-methyl-piperazin-1-ylmethyl)-thiazolo[3,2-a]pyrimidin-5-one 7-[5-(3-Chloro-4-fluoro-benzyl)-thiazol-2-yl]-6-hydroxy-2-(4-methyl-piperazin-1-ylmethyl)-thiazolo[3,2-a]pyrimidin-5-one 7-[5-(3,4-Difluoro-benzyl)-thiazol-2-yl]-6-hydroxy-2-(4-methyl-piperazin-1-ylmethyl)-thiazolo[3,2-a]pyrimidin-5-one

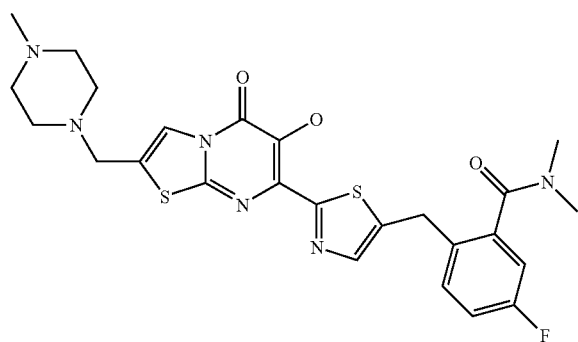 [SMILES: CN1CCN(Cc2cn3c(=O)c(O)c(-c4ncc(Cc5ccc(F)cc5C(=O)N(C)C)s4)nc3s2)CC1]

5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-N,N-dimethyl-benzamide

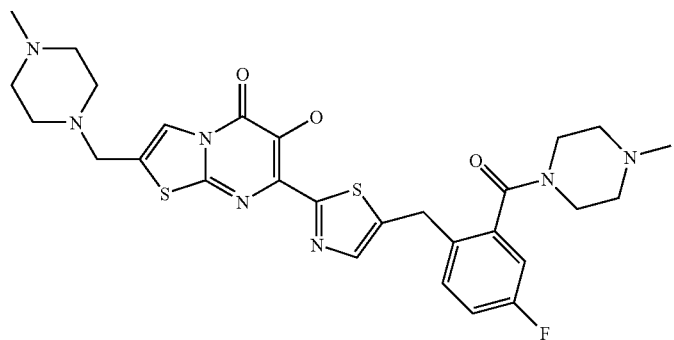 [SMILES: CN1CCN(Cc2cn3c(=O)c(O)c(-c4ncc(Cc5ccc(F)cc5C(=O)N5CCN(C)CC5)s4)nc3s2)CC1]

7-{5-[4-Fluoro-2-(4-methyl-piperazine-1-carbonyl)-benzyl]-thiazol-2-yl}-6-hydroxy-2-(4-methyl-piperazin-1-ylmethyl)-thiazolo[3,2-a]pyrimidin-5-one

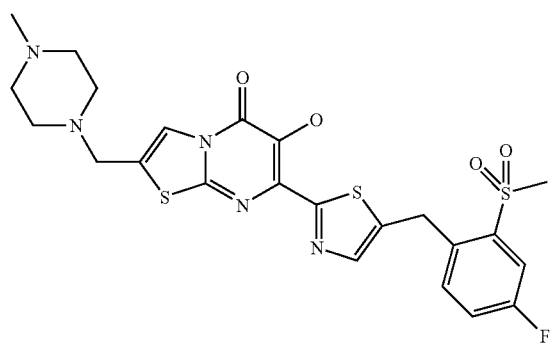 [SMILES: CN1CCN(Cc2cn3c(=O)c(O)c(-c4ncc(Cc5ccc(F)cc5S(C)(=O)=O)s4)nc3s2)CC1]

7-[5-(4-Fluoro-2-methanesulfonyl-benzyl)-thiazol-2-yl]-6-hydroxy-2-(4-methyl-piperazin-1-ylmethyl)-thiazolo[3,2-a]pyrimidin-5-one

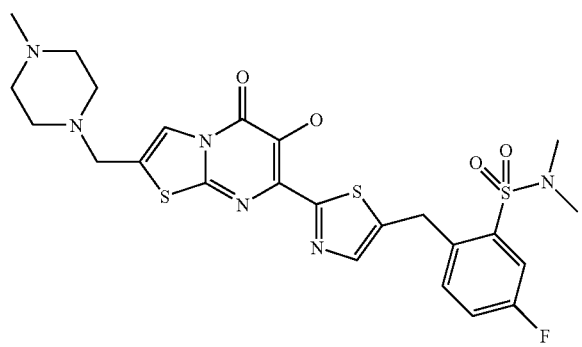 [SMILES: CN1CCN(Cc2cn3c(=O)c(O)c(-c4ncc(Cc5ccc(F)cc5S(=O)(=O)N(C)C)s4)nc3s2)CC1]

5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-N,N-dimethyl-benzenesulfonamide

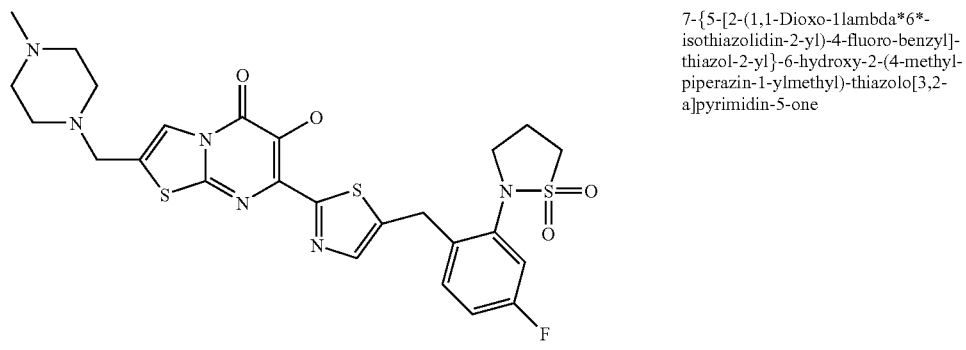

7-{5-[2-(1,1-Dioxo-1lambda*6*-isothiazolidin-2-yl)-4-fluoro-benzyl]-thiazol-2-yl}-6-hydroxy-2-(4-methyl-piperazin-1-ylmethyl)-thiazolo[3,2-a]pyrimidin-5-one

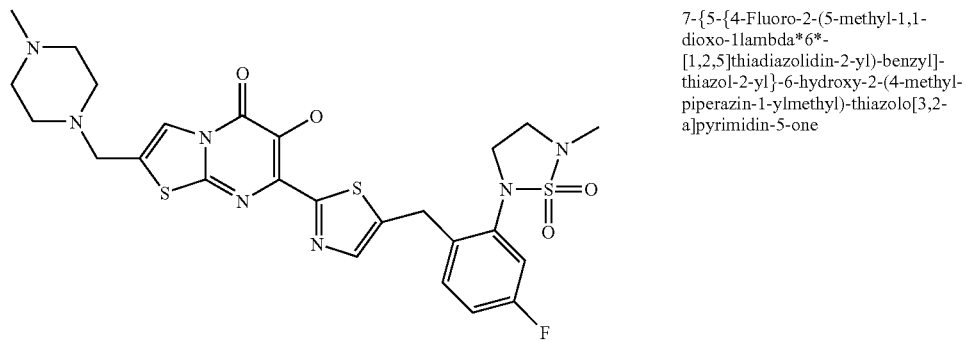

7-{5-{4-Fluoro-2-(5-methyl-1,1-dioxo-1lambda*6*-[1,2,5]thiadiazolidin-2-yl)-benzyl]-thiazol-2-yl}-6-hydroxy-2-(4-methyl-piperazin-1-ylmethyl)-thiazolo[3,2-a]pyrimidin-5-one

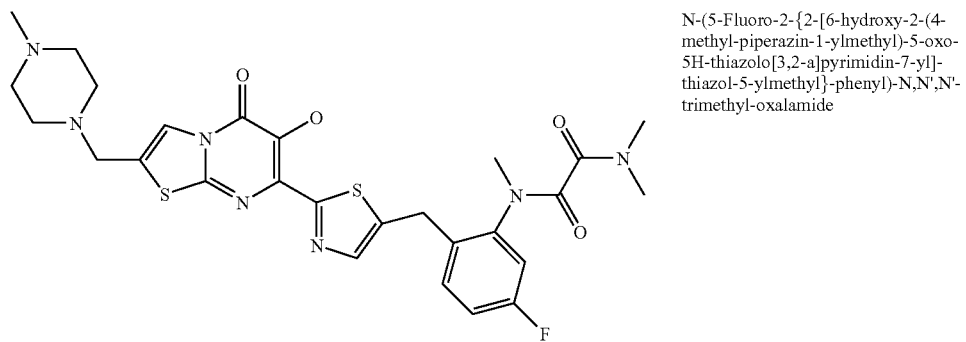

N-(5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-phenyl)-N,N',N'-trimethyl-oxalamide

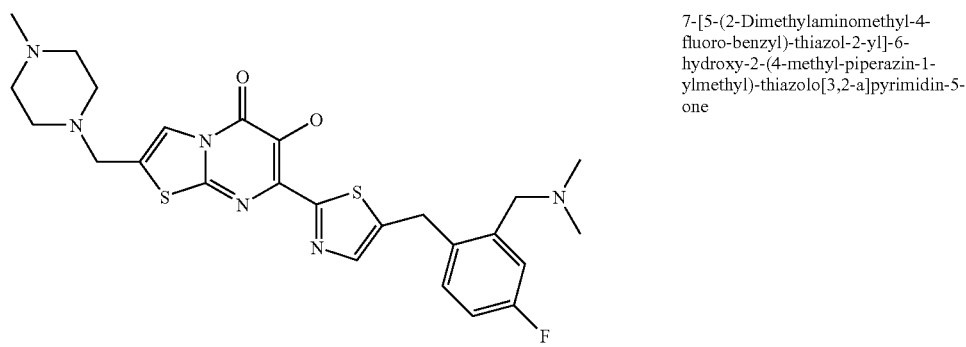

7-[5-(2-Dimethylaminomethyl-4-fluoro-benzyl)-thiazol-2-yl]-6-hydroxy-2-(4-methyl-piperazin-1-ylmethyl)-thiazolo[3,2-a]pyrimidin-5-one -continued

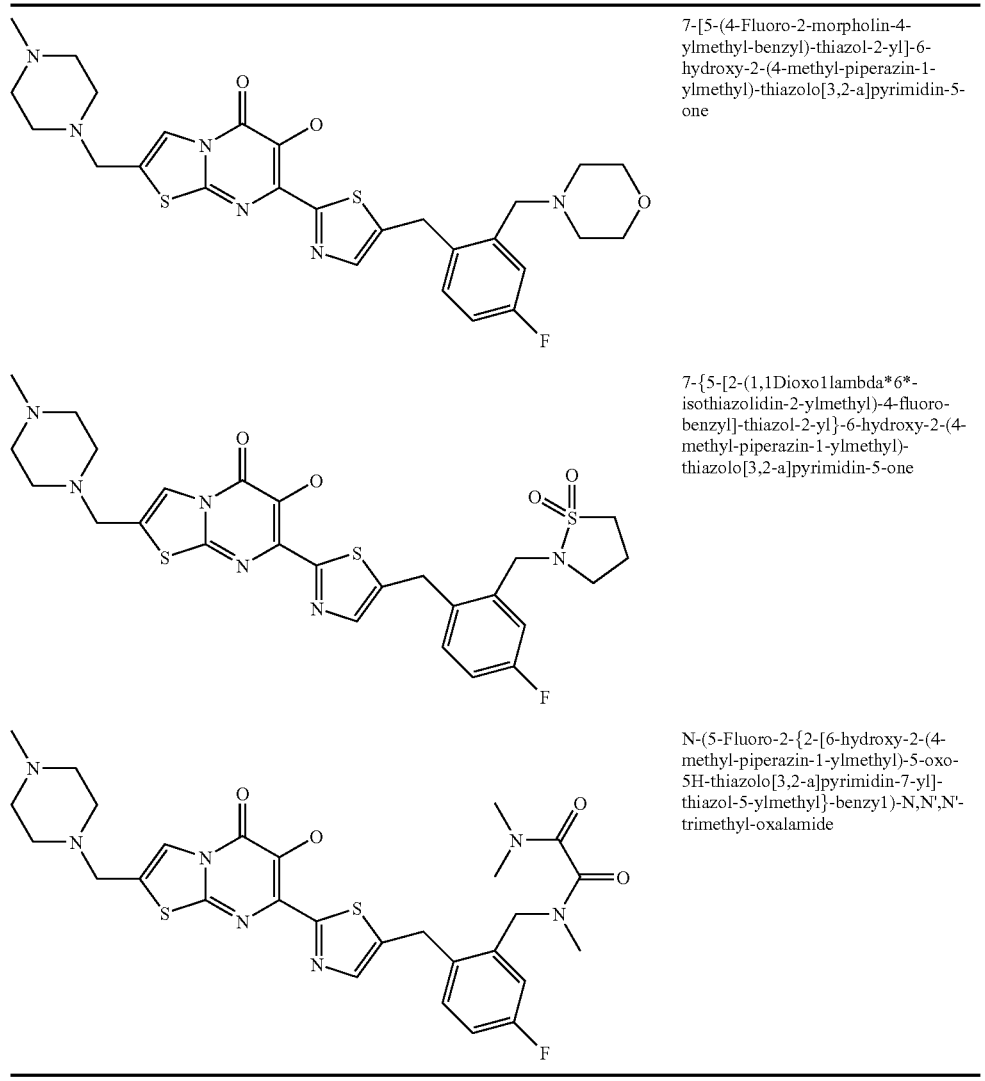

7-[5-(4-Fluoro-2-morpholin-4-ylmethyl-benzyl)-thiazol-2-yl]-6-hydroxy-2-(4-methyl-piperazin-1-ylmethyl)-thiazolo[3,2-a]pyrimidin-5-one 7-{5-[2-(1,1Dioxo1lambda*6*-isothiazolidin-2-ylmethyl)-4-fluoro-benzyl]-thiazol-2-yl}-6-hydroxy-2-(4-methyl-piperazin-1-ylmethyl)-thiazolo[3,2-a]pyrimidin-5-one N-(5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-benzyl)-N,N',N'-trimethyl-oxalamide Further preferred are compounds of Formula (I) as set out in the examples.

As used herein, the term "halo" or "halogen" refers to fluorine (fluoro), chlorine (chloro), bromine (bromo) or iodine (iodo).

As used herein, the terms "alkyl" and "alkylene" either used alone or in compound terms such as NH(alkyl) or N(alkyl)$_2$, refer respectively to monovalent and divalent straight chain or branched hydrocarbon groups, having 1 to 3, 1 to 6, or 1 to 10 carbon atoms as appropriate. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

As used herein, the term "alkenyl" refers to a straight chain or branched hydrocarbon groups having one or more double bonds between carbon atoms. Suitable alkenyl groups include, but are not limited to, ethenyl, allyl, propenyl, isopropenyl, butenyl, pentenyl and hexenyl.

The term "cycloalkyl" as used herein, refers to cyclic hydrocarbon groups. Suitable. cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "alkylaryl" includes, for example, benzyl.

The term "heterocycle" when used alone or in compound words includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic residue. The bonds between atoms may be saturated or unsaturated. Suitable heteroatoms include, O, N and S. Where two or more carbon atoms are replaced, this may be by two or more of the same heteroatom or by different heteroatoms. Suitable examples of heterocyclic groups may include pyrrolidinyl, piperidyl, piperazinyl, morpholino, quinolinyl, isoquinolinyl, thiomorpholino, dioxanyl, 2,2'-dimethyl-[1,3]-dioxolanyl, tetrahydropyranyl, tetrahydropyranyl, tetrahydropyrrolyl etc.

The term "heteroaryl" includes a 5- or 6-membered heteroaromatic ring containing one or more heteroatoms selected from O, N and S. Suitable examples of heteroaryl groups include furanyl, thiophenyl, tetrazolyl, 1,2,3-triazolyl, 1,2,4-triazolyl, imidazolyl, pyrazolyl, pyridinyl, pyrimidinyl, oxazolyl, oxadiazolyl, thioazolyl, thiodiazolyl etc. The heteroaromatic ring may be fused to a 5- or 6-membered aromatic or heteroaromatic ring to form a bicyclic aromatic ring system eg benzofuran.

Unless otherwise stated, each alkyl, alkylene, cycloalkyl, alkylaryl, aryl, heterocyclyl, or heteroaryl group may be optionally substituted with one or more of $C_1$-$C_3$alkyl, $C_3$-$C_6$cycloalkyl, $C_6$aryl, heterocyclyl, heteroaryl, $C_1$-$C_3$alkylOH, alkylaryl, OH, $OC_1$-$C_3$alkyl, halo, CN, $NO_2$, $CO_2H$, $CO_2C_1$-$C_3$alkyl, $CONH_2$, $CONH(C_{1-3}alkyl)$, $CON(C_1$-$C_3$alkyl$)_2$, trifluoromethyl, $NH_2$, $NH(C_1$-$C_3$alkyl) or $N(C_1$-$C_3$alkyl$)_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Each optional alkyl, cycloalkyl, alkylaryl, aryl, heterocyclyl, or heteroaryl substituent may also be optionally substituted.

Examples of optional substituents also include suitable nitrogen protecting groups (see "Protective Groups in Organic Synthesis" Theodora Greene and Peter Wuts, third edition, Wiley Interscience, 1999).

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" may include any pharmaceutically acceptable salt, hydrate or prodrug, or any other compound which upon administration to a subject, is capable of providing (directly or indirectly) a compound of formula I or an antibacterially active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine, and salts formed from ethylenediamine, choline or amino acids such as arginine, lysine or histidine. General information on types of pharmaceutically acceptable salts and their formation is known to those skilled in the art and is as described in general texts such as "*Handbook of Pharmaceutical salts*" P. H. Stahl, C. G. Wermuth, 1st edition, 2002, Wiley-VCH.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid This invention also encompasses pharmaceutical compositions containing prodrugs of compounds of formula I. This invention also encompasses methods of treating or preventing a viral infection in a subject by administering prodrugs of compounds of the formula I. Compounds of formula I having free amino, amido, hydroxy or carboxylic groups can be converted into prodrugs.

Prodrugs include compounds wherein an amino acid residue, or a polypeptide chain of two or more (eg, two, three or four) amino acid residues which are covalently joined to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

It will also be recognised that the compounds of formula I may possess asymmetric centres and are therefore capable of existing in more than one stereoisomeric form.

The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

Preferably, the viral infection of the second and third aspects is a HIV or SIV infection.

More preferably, the HIV or SIV infection comprises a viral strain resistant to other integrase inhibitors such as Isentrass (raltregavir, MK-0158) or elvitegravir. Even more preferably, the viral strain comprises HIV integrase enzyme containing the Q148H/G140S double mutation, N155H/E92Q double mutation, the F121Y/T124K double mutation or the Q148K/G140A/E138A triple mutation.

In a preferred form of the second and third aspects of the present invention, the compound of formula (I) is co-administered with Raltegravir. The compound of formula (I) can be administered simultaneously with Raltegravir, or the compound of formula (I) can be administered before or after the administration of Raltegravir provided they are in the same course of treatment as would be understood by the person skilled in the art.

In a fourth aspect, the present invention provides pharmaceutical composition comprising a compound according to the first aspect and a pharmaceutically acceptable carrier, diluent or excipient.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, parenterally, such as by subcutaneous, intravenous, intramuscular, or intracisternal injection or infusion techniques (e.g., as sterile injectable aqueous or non-aqueous solutions or suspensions).

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female.

The term "effective amount" means the amount of the subject composition that will elicit the biological or medical response of a tissue, system, animal or human that is being sought by the researcher, veterinarian, medical doctor or other clinician.

As would be understood by those skilled in the art of treating viral infections, and particularly HIV infections, the term "treatment" does not necessarily mean that the viral infection is completely cured. The term "treatment" encompasses any reduction in the viral load and/or inhibition of replication in the subject being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical composition and method of the present invention may further comprise other therapeutically active compounds which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require HIV inhibition or HIV integrase enzyme inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order that the nature of the present invention may be more clearly understood preferred forms thereof will now be described by reference to the following non-limiting Examples.

1. ROUTES OF SYNTHESIS

1.1 For Core Formation

Scheme 1: Preparation of the pyrimidinone bicyclic system

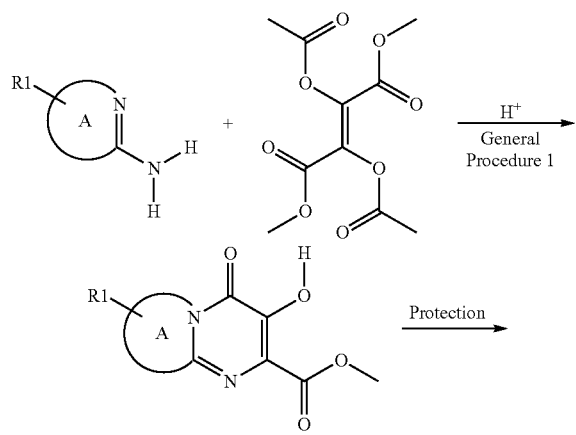

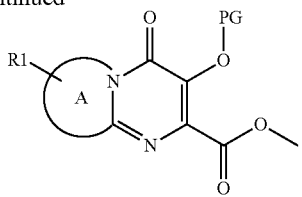

General Procedure 1: *Adaption of Organic Preparations and Procedures International*, 22(4), 1990, 532-534

International Patent Application No. PCT/AU2007/001980 in the name of Avexa.

The amino compound can be reacted as in scheme 1 with the fumarate derivative or suitable analogues of fumarate where for example the acetyl groups can be replaced by other suitable leaving groups such as tosyl or mesyl. The reaction can be carried out in a suitable solvent such as methanol, DME, DMA, DMSO, chloroform, THF or dioxane. The reaction can be heated or subject to microwave irradiation (see for example B. R. Roberts & C. R. Strauss, Acc. Chem. Res. 2005, 38, 653-661, "Toward Rapid, 'Green' Predictable Microwave-assisted Synthesis"). The reaction can be performed in the absence or presence of catalytic amounts of acid or base.

1.2 Generic Schemes

Azole Formation

1.2.1 For H1=1,3-oxazole and 1,3-thiazole

Scheme 2: Preparation of the 1,3-oxazole and 1,3-thiazole via Gabriel or Robinson-Gabriel method

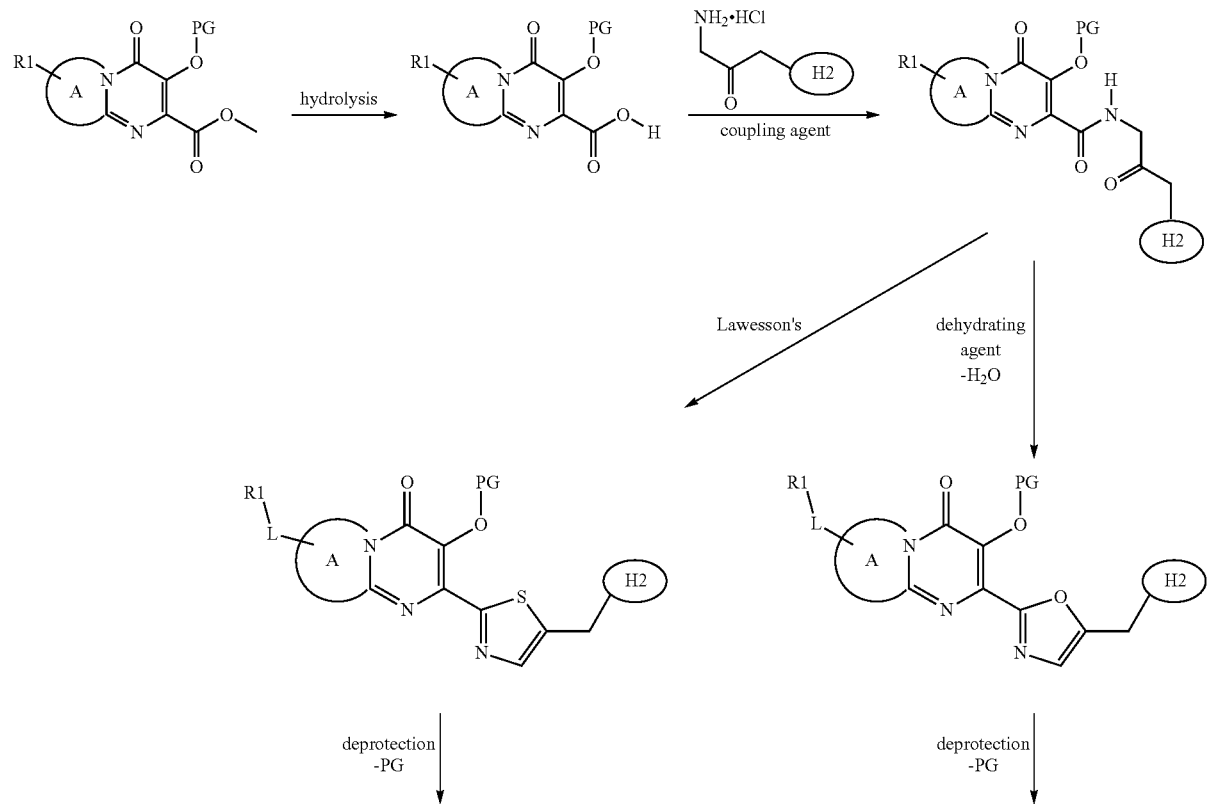

-continued

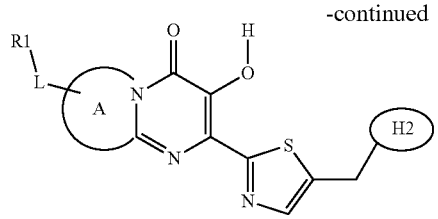
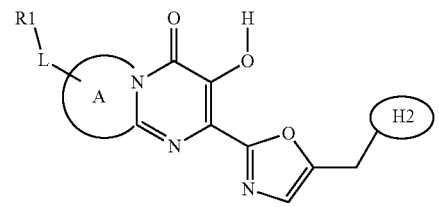

International Patent Application No. PCT/AU2007/001980 in the name of Avexa.

Editor R. R. Gupta, Microwave-Assisted Synthesis of Heterocycles, Springer Berlin/Heidelberg. ISSN: 1861-9282 (Print) 1861-9290 (Online), 2006

Scheme 3: Preparation of the imidazole

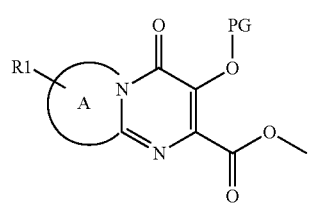

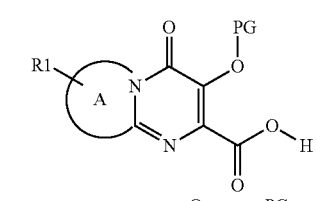

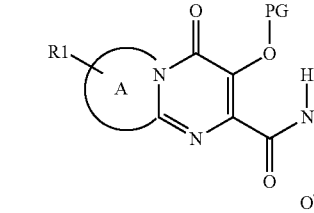

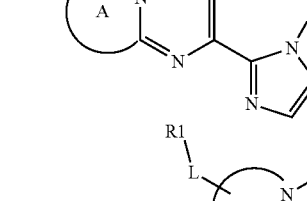

Editor R. R. Gupta, Microwave-Assisted Synthesis of Heterocycles, Springer Berlin/Heidelberg. ISSN: 1861-9282 (Print) 1861-9290 (Online), 2006

Scheme 4: Preparation of the 1,3-thiazole via Hantzsch method

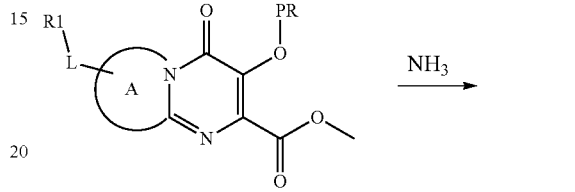

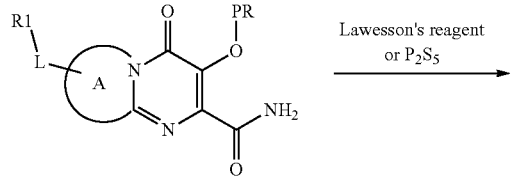

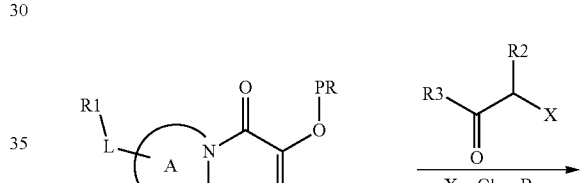

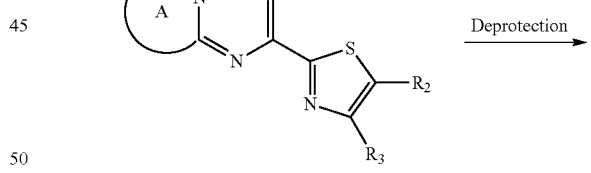

Wawzonek, O., In; Heterocyclic Compounds, John Wiley and Sons, New York, 1975.

Tetrahedron Letters, 1994, 35(16), 2473-2476

Bioorg. Med. Chem. Chem. Lett. 2003, 13 (24), 4467-72.

Scheme 5: Alternative preparation of the 1,3-thiazole
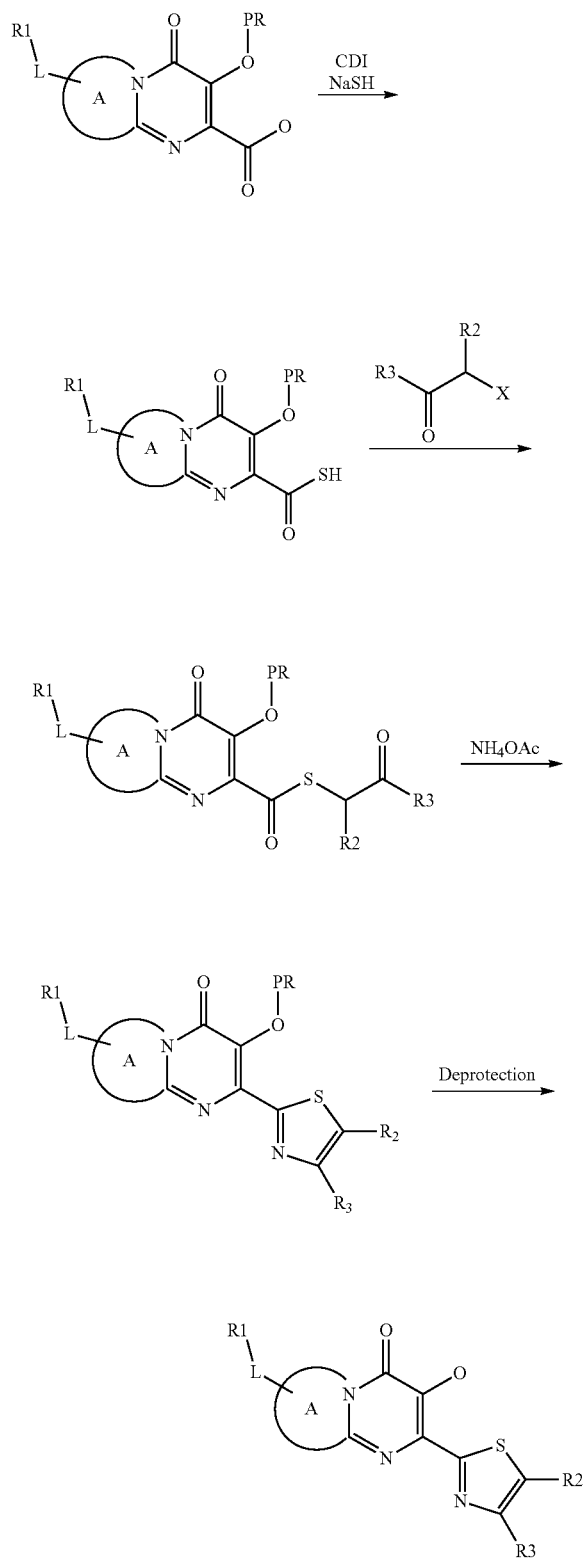
Scheme 6: Alternative preparation of the 1,3-thiazole from aldehyde
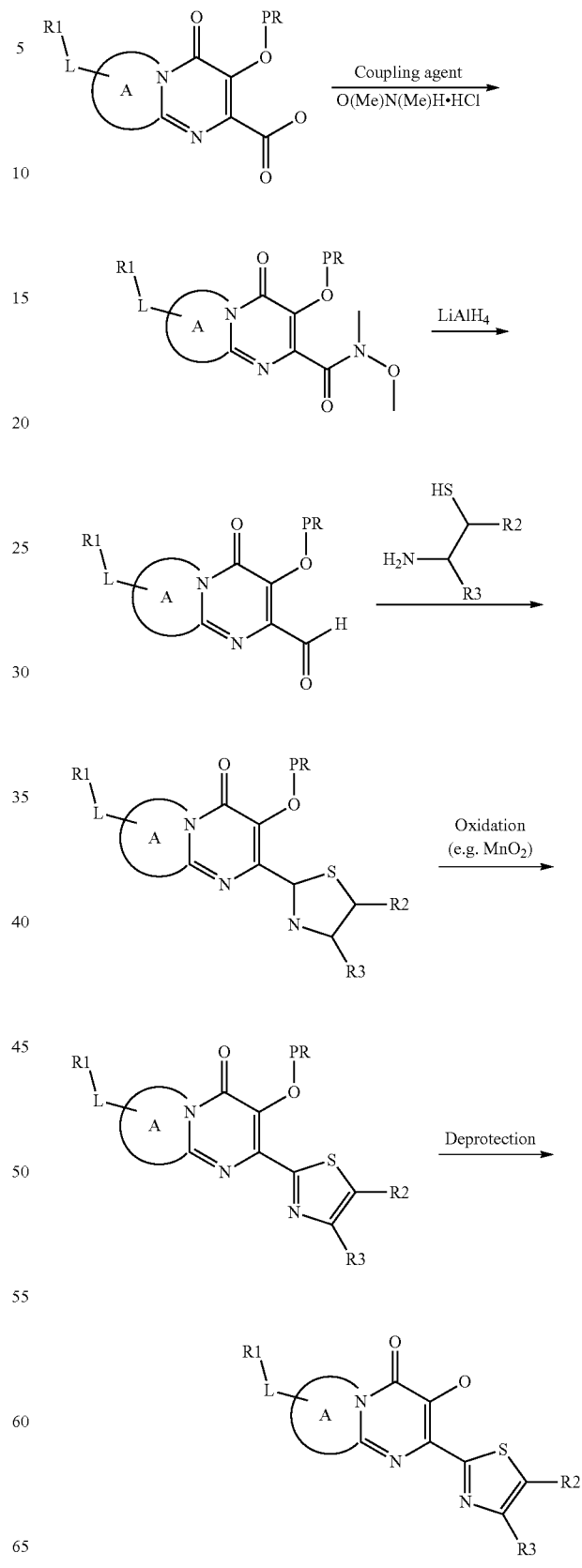
*Tetrahedron.* 2001, 57 (20), 4323-4336.
*Org. Lett.* 2003, 5(16), 2785-88;
*Synthesis.* 1976, 696-697

1.2.2 For H1=1,3,4-oxadiazole and 1,3,4-oxathiazole
Scheme 7: Preparation of the 1,3,4-oxadiazole and 1,3,4-thiadiazole
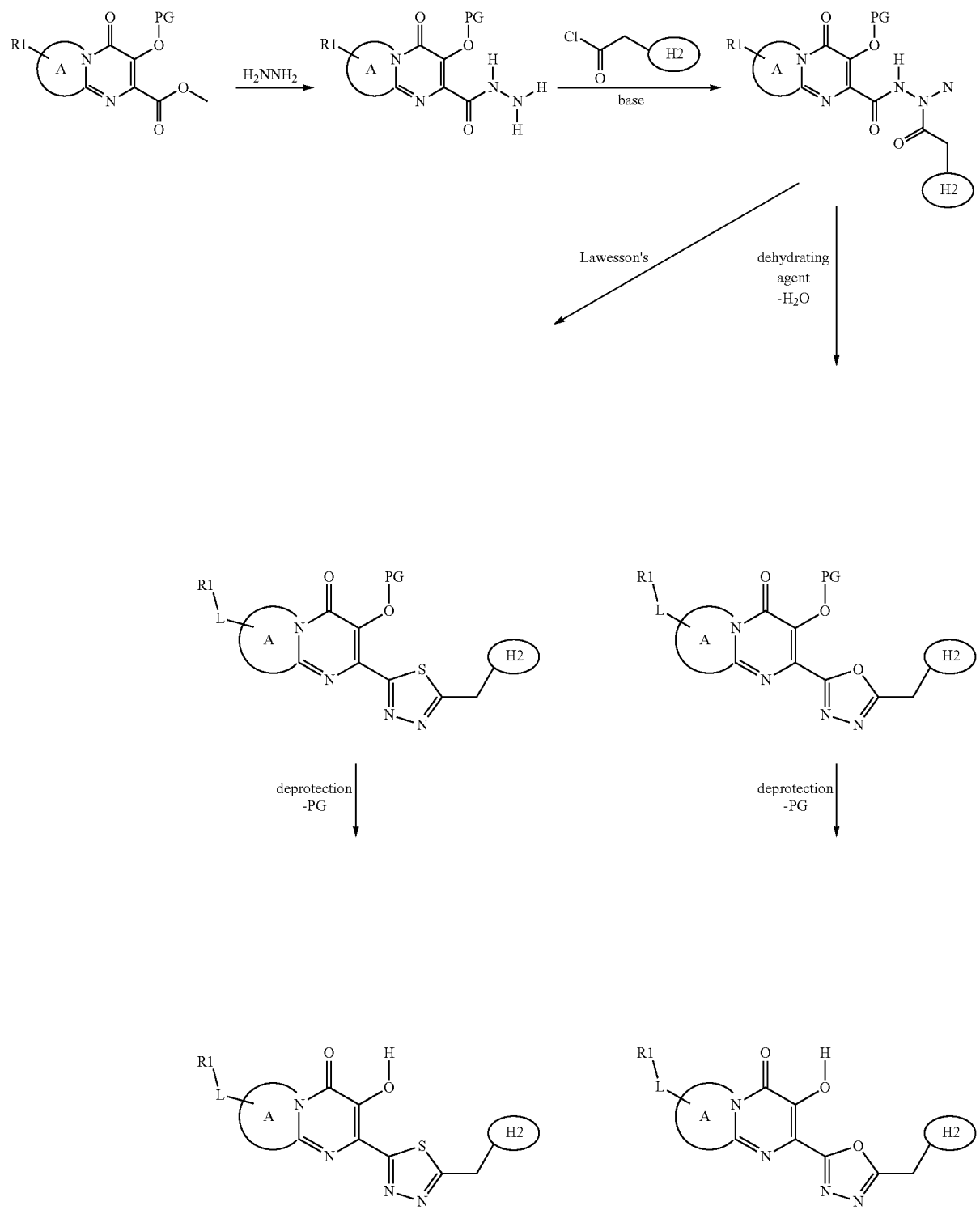
International Patent Application No. PCT/AU2007/001980 in the name of Avexa.

1.2.3 For H1=1,2,4-oxadiazole
Scheme 8: Preparation of the 1,2,4-oxadiazole
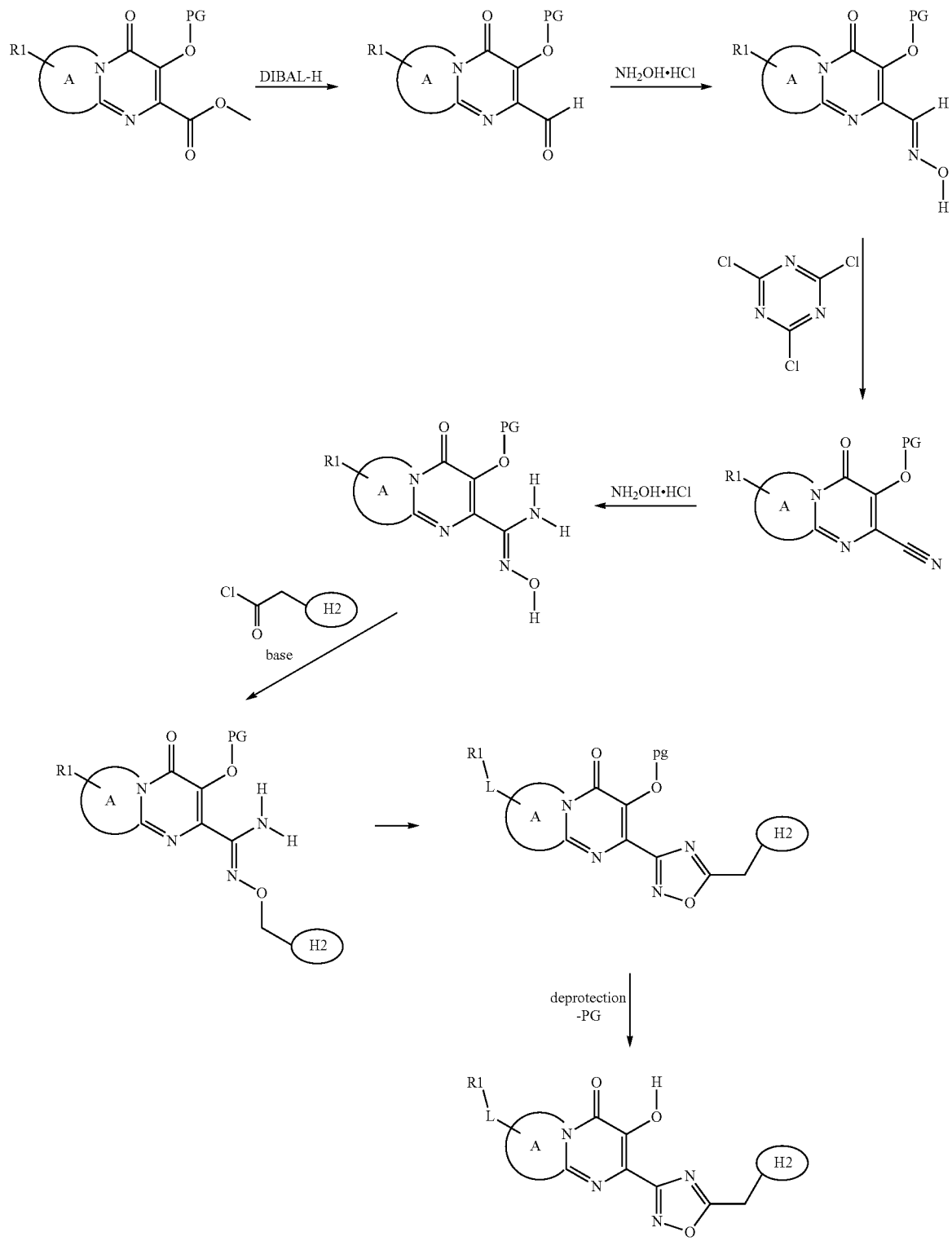
International Patent Application No. PCT/AU2007/001980 in the name of Avexa.

33

Scheme 9: Preparation of the 1,2,4-oxadiazole (reversed roles)

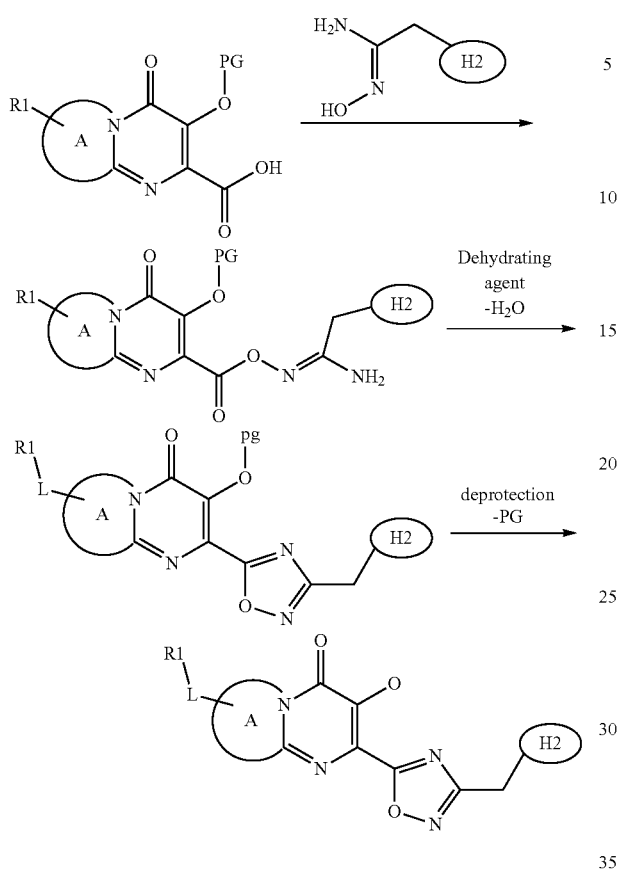

International Patent Application No. PCT/AU2007/001980 in the name of Avexa.

1.3 Generic Schemes

Preparation of Ketoamines

Scheme 10: Preparation of 1-Amino-3-aryl-propan-2-one hyrdrochloride

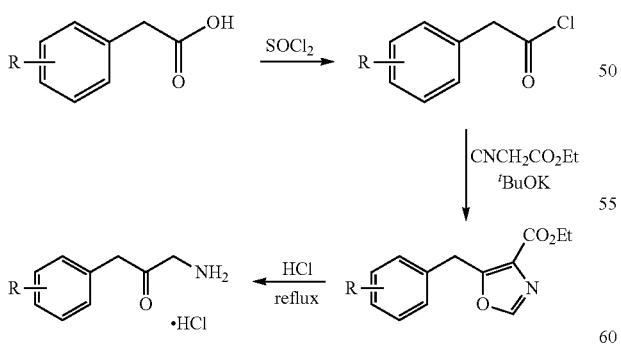

*Tetrahedron,* 1994, 50 (21), 6287-6298 and *Chem. Pharm. Bull.* 1984, 32 (7), 2536-2543

Examples: R=3-F, 4-Cl; 3-Cl, 4-F

R=4-F; 2,4-$Cl_2$ International Patent Application No. PCT/AU2007/001980 in the name of Avexa.

34

R=4-Cl: *Chem. Pharm. Bull.* 1984, 32 (7), 2536-2543
R=2-NO2: *Tetrahedron* 1994, 50(21) 6287-6298

Scheme 11: Alternative preparation of 1-Amino-3-aryl-propan-2-one hyrdrochloride

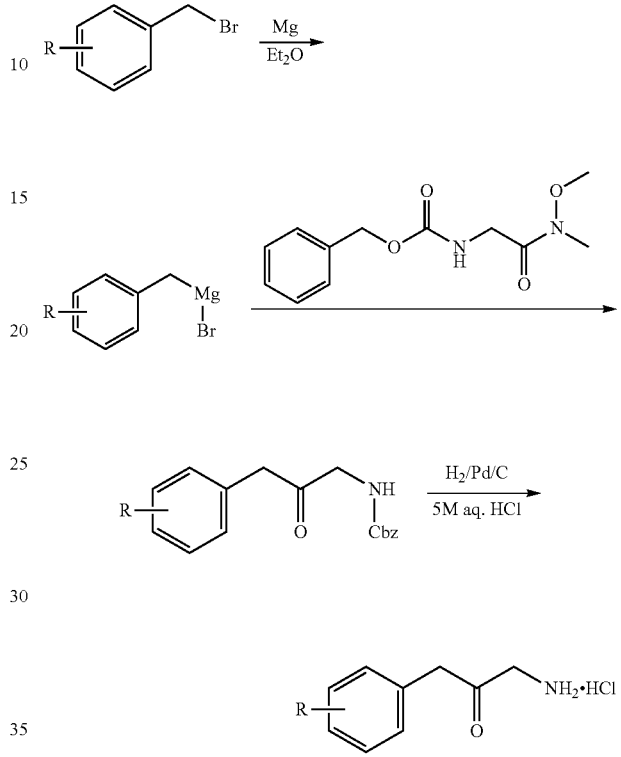

US20040229909; 'Antiviral agent", Shionogi

Scheme 12: Alternative preparation of 1-Amino-3-aryl-propan-2-one hyrdrochloride

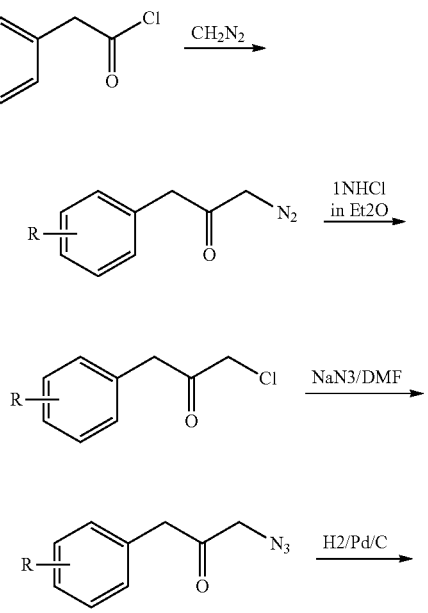

-continued
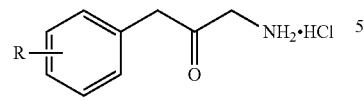
Journal of Organic Chemistry (2003), 68(7), 2798-2802. (for ketoazide from chloroketone)
Scheme 13: Alternative preparation of 1-Amino-3-aryl-propan-2-one hyrdrochloride
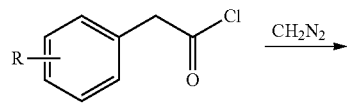
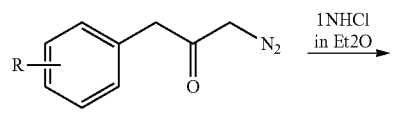
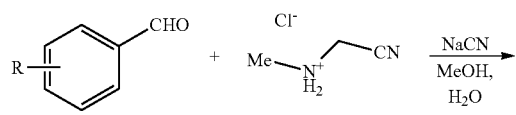
Scheme 14: Preparation of o-ester ketoamine
-continued
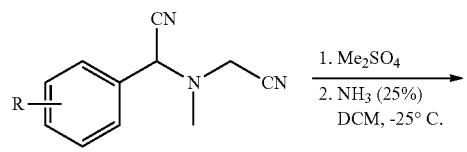
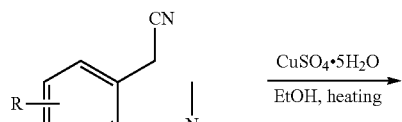
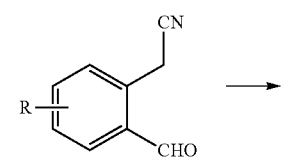
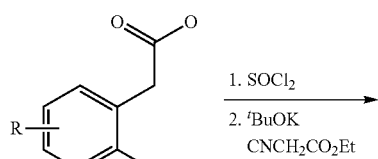
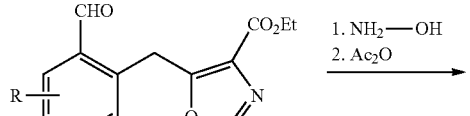
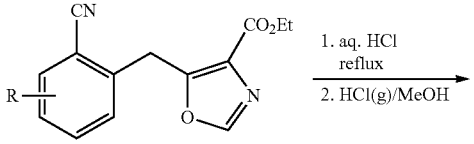
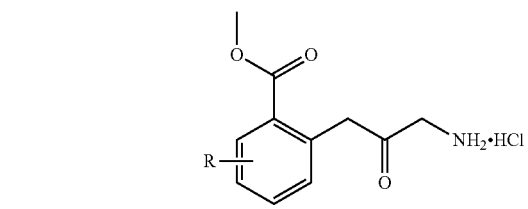
J. Org. Chem. 1991, 56(24), 6933-6937

Scheme 15: Preparation of o-aminomethyl ketoamine
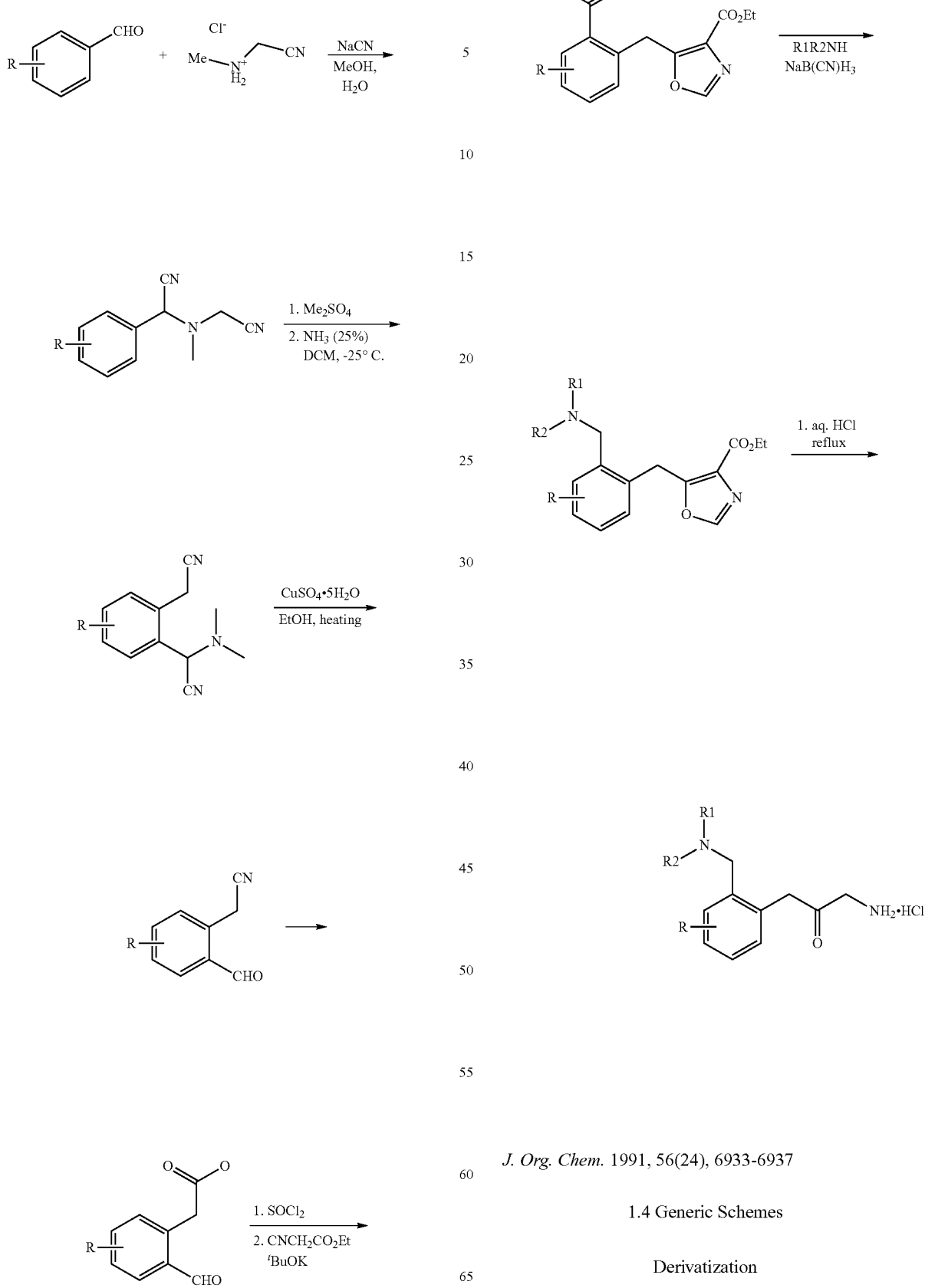
*J. Org. Chem.* 1991, 56(24), 6933-6937
1.4 Generic Schemes
Derivatization
As Scheme 15, but Derivatization is in a Different Position

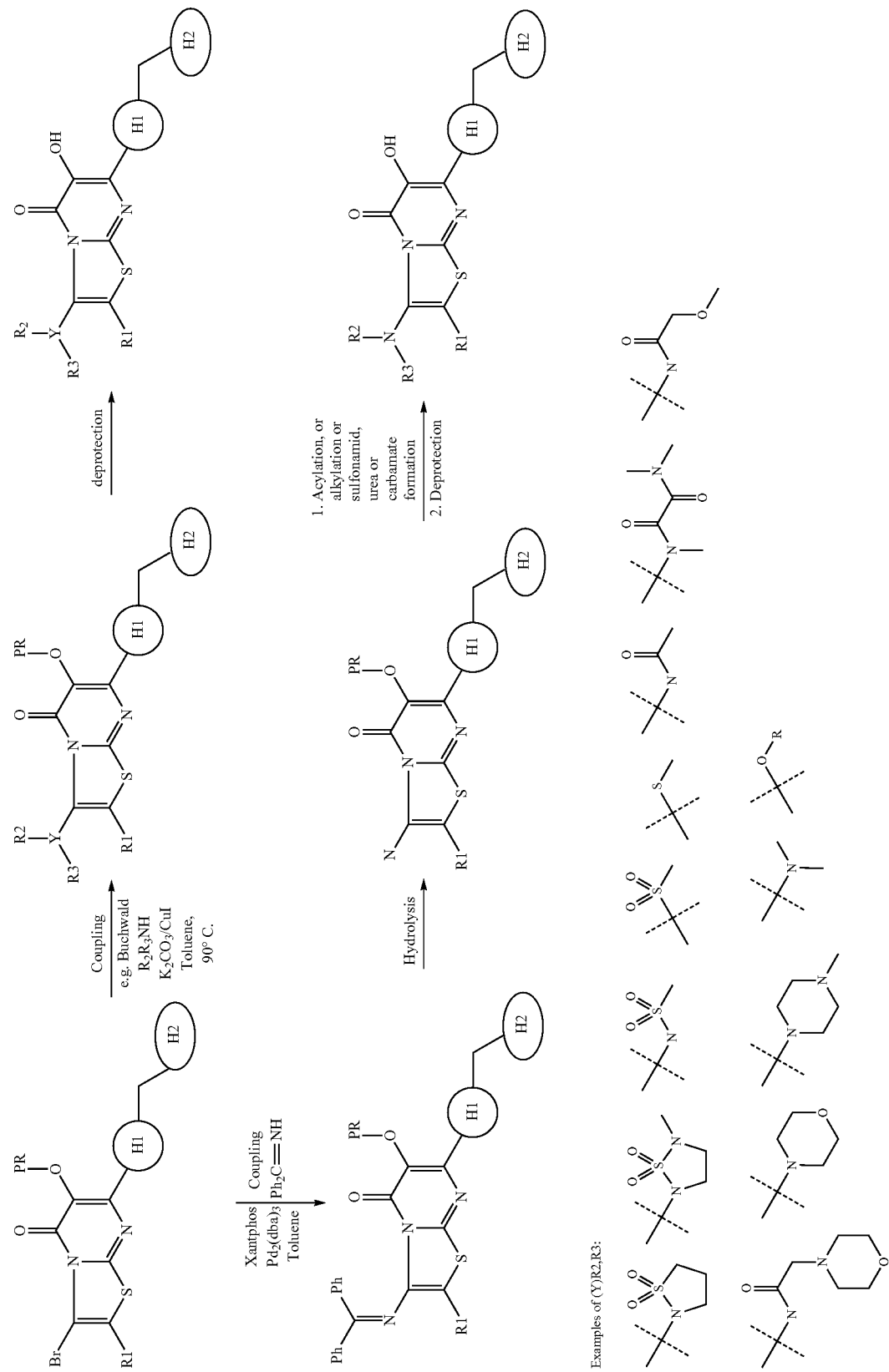

International Patent Application No. PCT/AU2007/001980 in the name of Avexa.
Scheme 17: Derivatization of thiazole examples: Variation at position 2
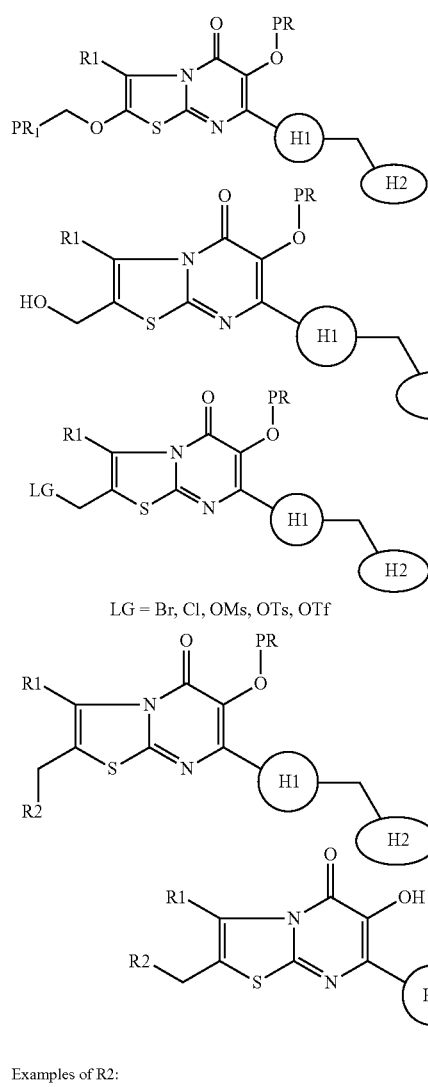
Scheme 18: Derivatization of position 2 of thiazole compounds
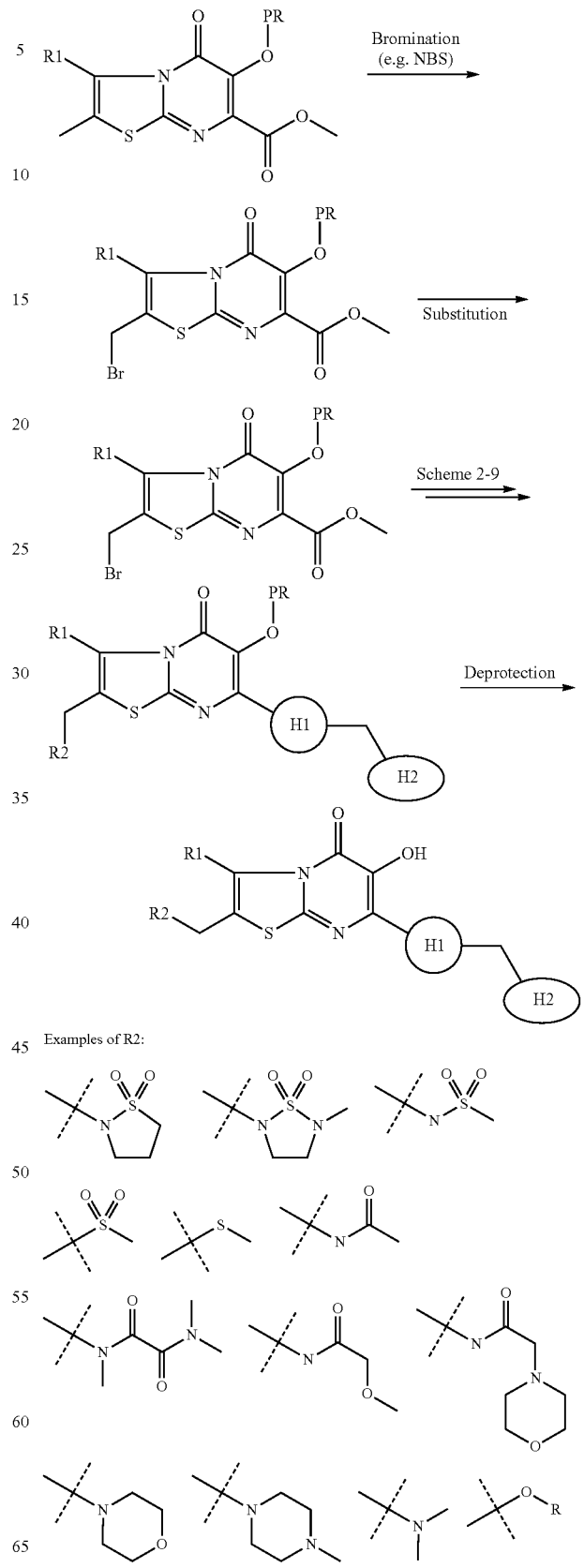

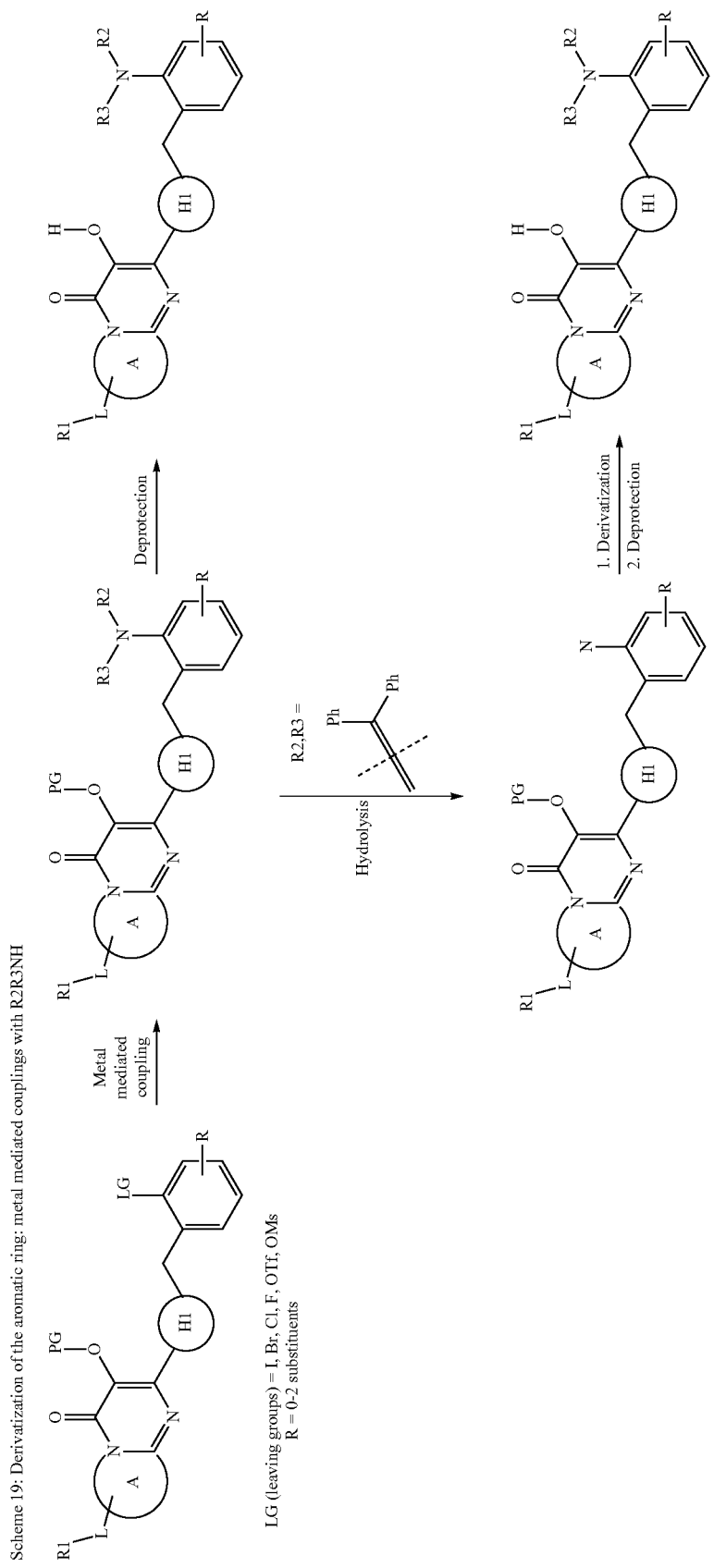
Scheme 19: Derivatization of the aromatic ring: metal mediated couplings with R2R3NH
LG (leaving groups) = I, Br, Cl, F, OTf, OMs
R = 0-2 substituents

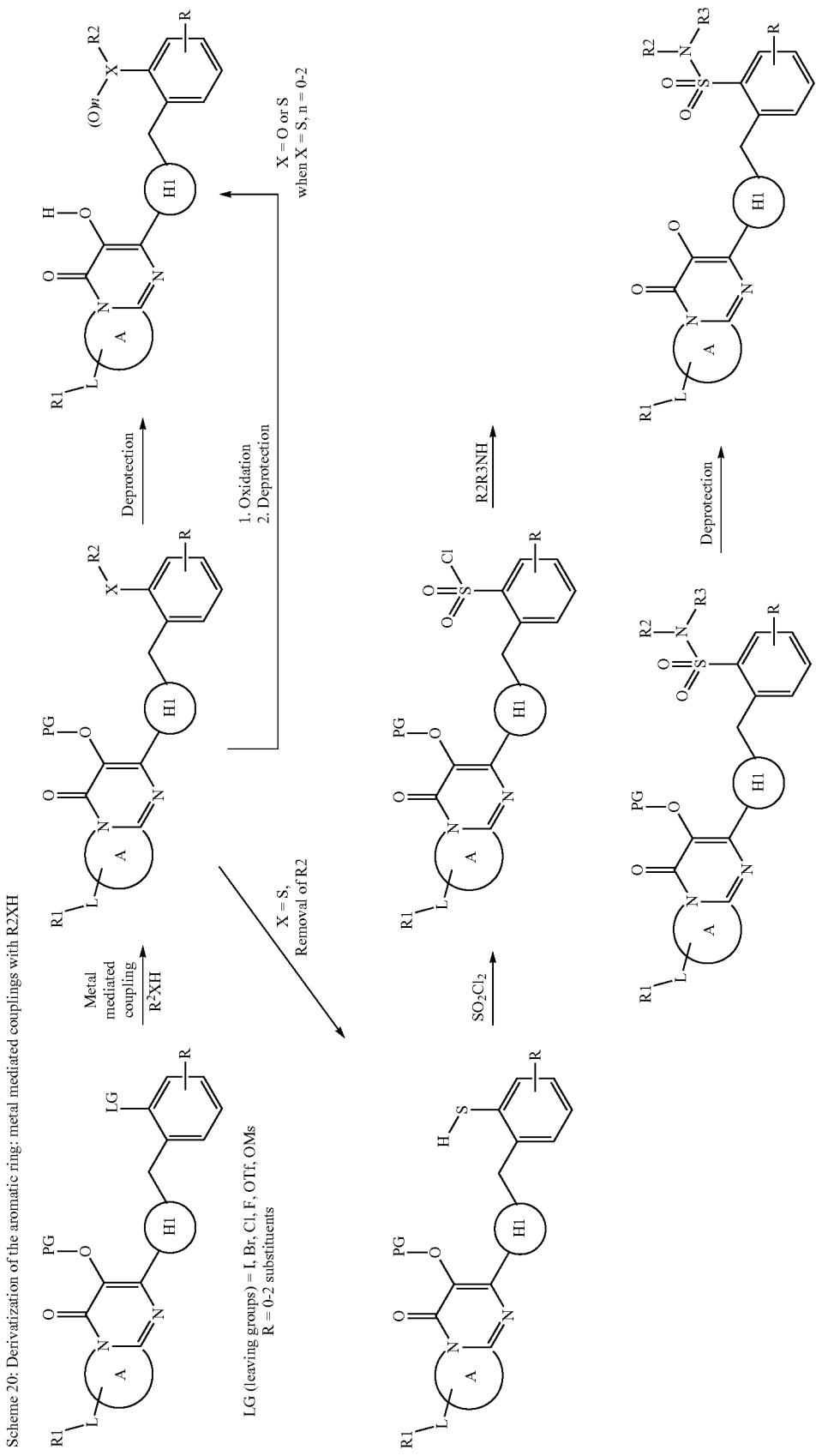
Scheme 20: Derivatization of the aromatic ring: metal mediated couplings with R2XH
LG (leaving groups) = I, Br, Cl, F, OTf, OMs
R = 0-2 substituents Scheme 21: Derivatization of the aromatic ring: metal mediated couplings with CO2
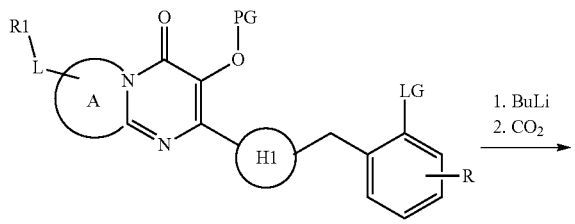
LG (leaving groups) = I, Br, Cl, F, OTf, OMs
R = 0-2 substituents
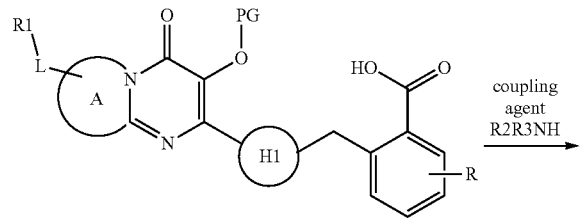
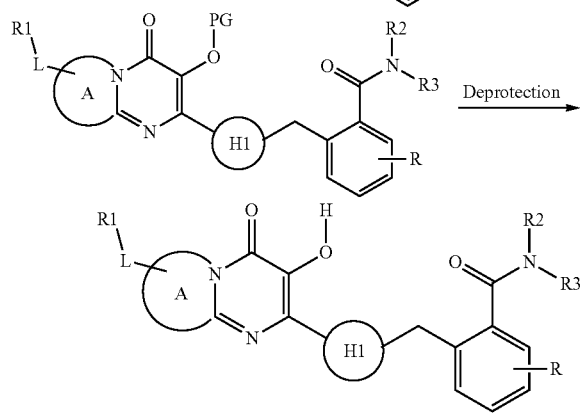
Scheme 22: Derivatization of the aromatic ring: metal mediated couplings with DMF
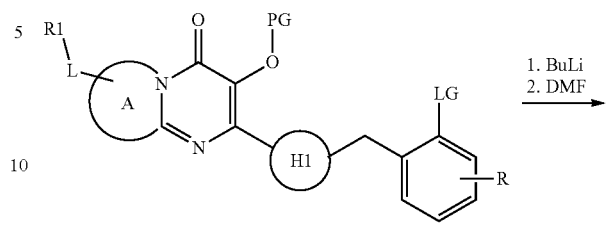
LG (leaving groups) = I, Br, Cl, F, OTf, OMs
R = 0-2 substituents
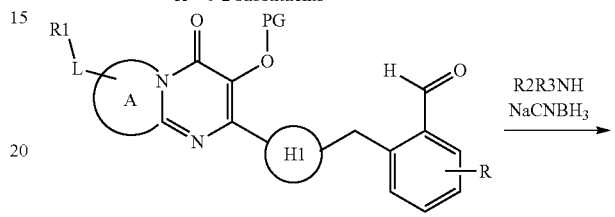
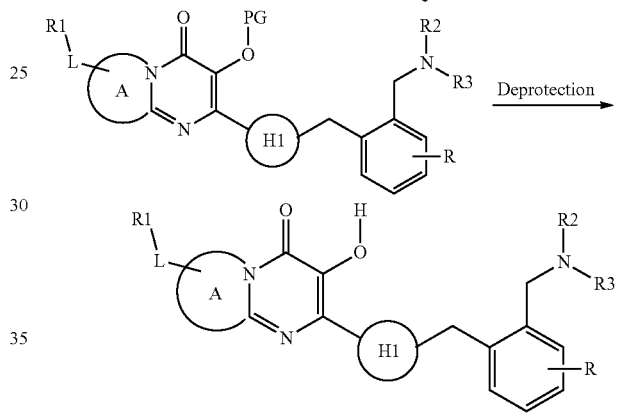
Scheme 23: Derivatization of the aromatic ring: amide formation in ortho position
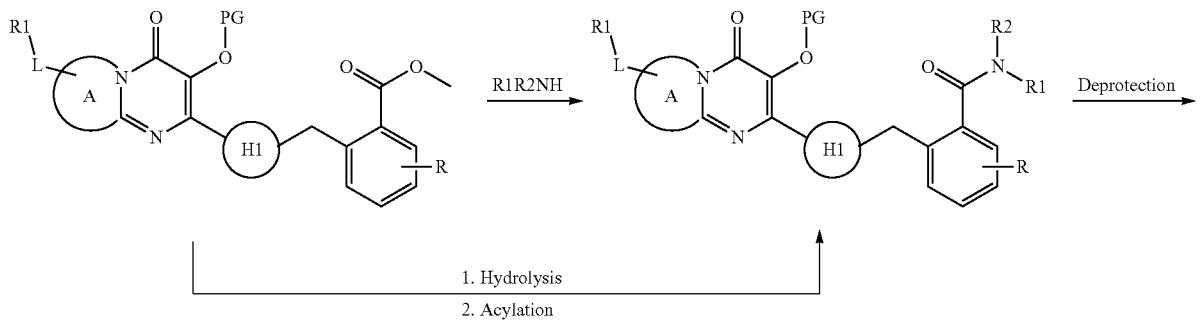
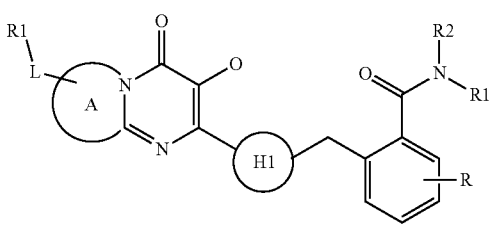

49

Scheme 24: Derivatization of the aromatic ring: amine in ortho position

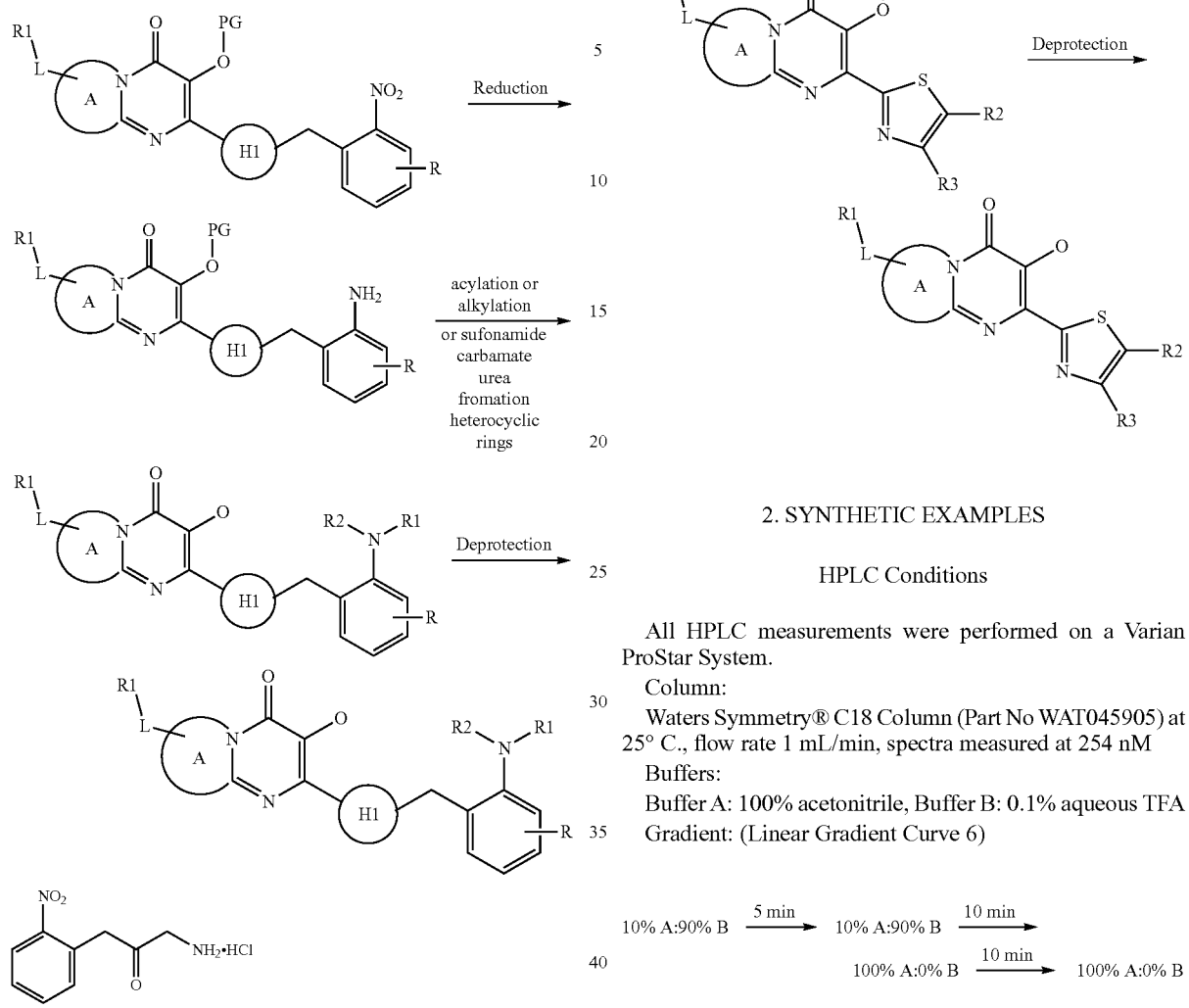

Tetrahedron (1994), 50(21), 6287-98.

Scheme 25: Derivatization of thiazole by coupling

50

2. SYNTHETIC EXAMPLES

HPLC Conditions

All HPLC measurements were performed on a Varian ProStar System.

Column:
Waters Symmetry® C18 Column (Part No WAT045905) at 25° C., flow rate 1 mL/min, spectra measured at 254 nM Buffers:
Buffer A: 100% acetonitrile, Buffer B: 0.1% aqueous TFA
Gradient: (Linear Gradient Curve 6)

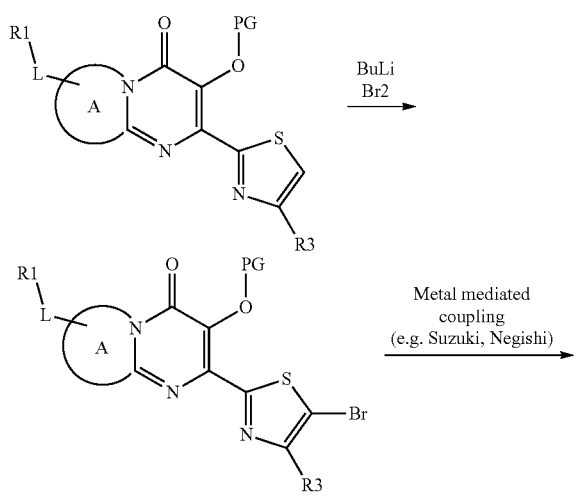

Example 1

Preparation of 6-benzyloxy-2-methyl-5-oxo-5H-thiazolo[3,2-a]pyrimidine-7-carboxylic acid

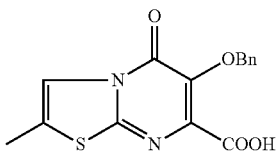 [SMILES: Cc1cn2c(=O)c(OCc3ccccc3)c(C(=O)O)nc2s1]

The titled compound was prepared by adapting methods described in Example 8.1-8.2 of PCT/AU2007/001980 using as a starting material 6-Hydroxy-2-methyl-5-oxo-5H-thiazolo[3,2-a]pyrimidine-7-carboxylic acid methyl ester prepared according to example 1(a).

$^1$H NMR (300 MHz, DMSO-d$^6$) 2.43 (d, J=1.5 Hz, 3H), 5.09 (s, 2H), 7.31-7.45 (m, 5H), 7.93 (q, J=1.5 Hz, 1H), 13.73 (s, 1H)

MS (ESI$^-$) m/z 315 (M–1)

Example 1(a)

Preparation of 6-Hydroxy-2-methyl-5-oxo-5H-thiazolo[3,2-a]pyrimidine-7-carboxylic acid methyl ester

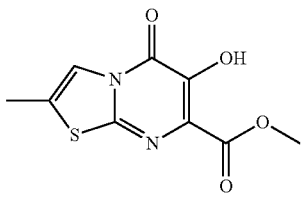

2-Amino-5-methylthiazole (11.7 g, 103 mmol), DAF (29.5 g, 114 mmol) and p-TosOH (3.1 g, 16 mmol) were combined and heated at 120° C. for 4 hours. After cooled down to room temperature, EA (20 ml) was added and sonicated for 2 minutes. The solids were collected by filtration, washed by cold methanol and dried in vacuo to afford the thiazole core (10 g, yield 40%).

$^1$H NMR (300 MHz, DMSO-d$^6$) δ 2.41 (d, J=1.5 Hz, 3H), 3.84 (s, 3H), 7.81 (q, J=1.4 Hz, 1H), 10.14-10.29 (brs, 1H).

MS (ESI$^+$) m/z 263 (M+23)

Example 2

Preparation of 6-benzyloxy-2-methyl-5-oxo-5H-thiazolo[3,2-a]pyrimidine-7-carboxylic acid [3-(4-fluoro-phenyl)-2-oxo-propyl]-amide

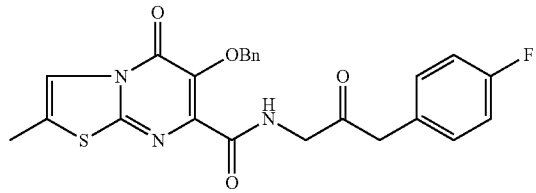 [SMILES: Cc1cn2c(=O)c(OCc3ccccc3)c(C(=O)NCC(=O)Cc3ccc(F)cc3)nc2s1]

To a solution of the product of example 1 (2.4 mmol) in THF (10 ml) was added compound 1-amino-3-(4-fluoro-phenyl)-propan-2-one hydrochloride (1.0 g, 4.9 mmol), EDCI·HCl (560 mg, 2.9 mmol), HOBt (400 mg, 2.9 mmol) and TEA (1 g, 9.9 mmol), successively at room temperature. The mixture was stirred overnight, after which saturated sodium bicarbonate was added and then extracted with ethyl acetate. The extracts were combined, washed with brine, and then dried over sodium sulfate. The product was purified by column chromatography to give the desired product.

$^1$H NMR (300 MHz, DMSO-d$^6$) 2.45 (d, J=1.5 Hz, 3H), 3.84 (s, 2H), 4.19 (d, J=5.9 Hz, 2H), 5.09 (s, 2H), 7.14 (t, J=9.0 Hz, 2H), 7.22 (dd, J=5.6, 8.8 Hz, 2H), 7.28-7.38 (m, 3H), 7.48 (dd, J=2.1, 7.6 Hz, 2H), 7.93 (q, J=1.5 Hz, 1H), 8.74 (t, J=5.7 Hz, 1H)

MS (ESI$^+$) m/z 464 (M−1)

Example 3

Preparation of 6-benzyloxy-7-[5-(4-fluoro-benzyl)-thiazol-2-yl]-2-methyl-thiazolo[3,2-a]pyrimidin-5-one

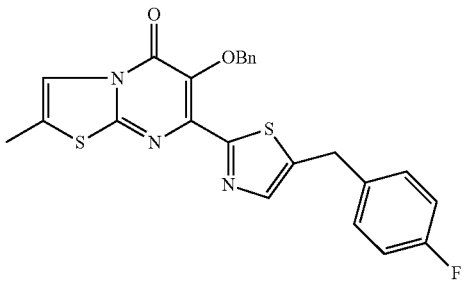 [SMILES: Cc1cn2c(=O)c(OCc3ccccc3)c(-c3ncc(Cc4ccc(F)cc4)s3)nc2s1]

The product from example 1 (0.23 mmol) and Lawensson's reagent (120 mg, 0.3 mmol) were mixed with toluene (10 mL) and refluxed for 12 h. The reaction mixture was concentrated in vacuo and flash chromatography afforded the desired thiazole product.

$^1$H NMR (300 MHz, DMSO-d$^6$) 2.44 (d, J=1.5 Hz, 3H), 4.25 (s, 2H), 5.18 (s, 2H), 7.17 (t, J=8.9 Hz, 2H), 7.30-7.40 (m, 5H), 7.46-7.52 (m, 2H), 7.87 (s, 1H), 7.89 (q, J=1.6 Hz, 1H).

MS (ESI$^+$) m/z 486 (M+23)

Example 4

Preparation of 7-[5-(4-Fluoro-benzyl)-thiazol-2-yl]-6-hydroxy-2-methyl-thiazolo[3,2-a]pyrimidin-5-one

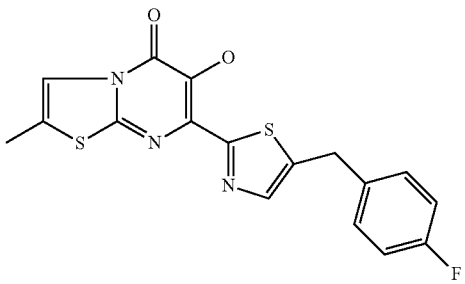 [SMILES: Cc1cn2c(=O)c(O)c(-c3ncc(Cc4ccc(F)cc4)s3)nc2s1]

To a solution of the product of example 3 (0.135 mmol) in CH$_2$Cl$_2$ (4 ml) was added FeCl$_3$ (66 mg, 0.402 mmol) at room temperature. The mixture was stirred at room temperature for 2 hours, after which CH$_2$Cl$_2$ was evaporated under reduced pressure and ethyl acetate (30 ml) was added. Then the mixture was washed by 1N HCl (10 ml), H$_2$O (10 ml) and brine (10 ml) successively, dried over Na$_2$SO$_4$ and concentrated into about 1 ml. The resulting solids were collected by filtration and washed with cold ethyl acetate (2-3 ml) to give the desired product $^1$H NMR (300 MHz, DMSO-d$^6$) 2.40 (d, J=1.5 Hz, 3H), 4.29 (s, 2H), 7.17 (t, J=8.8 Hz, 2H), 7.38 (dd, J=5.6, 8.6 Hz, 2H), 7.81 (q, J=1.4 Hz, 1H), 7.91 (s, 1H), 11.34 (s, 1H)

MS (ESI$^+$) m/z 396 (M+23)

HPLC 94.2%

Example 5

Preparation of 6-benzyloxy-2-methyl-5-oxo-5H-thiazolo[3,2-ba]pyrimidine-7-carboxylic acid [3-(4-chloro-phenyl)-2-oxo-propyl]-amide

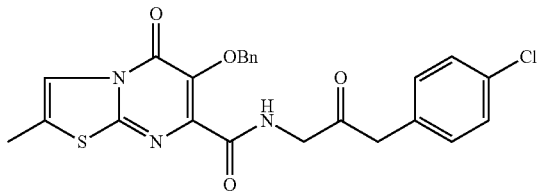 [SMILES: Cc1cn2c(=O)c(OCc3ccccc3)c(C(=O)NCC(=O)Cc3ccc(Cl)cc3)nc2s1]

Adapted from example 2 using the product of example 1 and 1-amino-3-(4-chloro-phenyl)-propan-2-one hydrochloride.
$^1$H NMR (300 MHz, DMSO-d$^6$) 2.45 (d, J=1.5 Hz, 3H), 3.86 (s, 2H), 4.19 (d, J=5.7 Hz, 2H), 5.09 (s, 2H), 7.22 (d, J=8.5 Hz, 2H), 7.29-7.41 (m, 5H), 7.48 (dd, J=2.2, 7.5 Hz, 2H), 7.93 (q, J=1.5 Hz, 1H), 8.75 (t, J=5.7 Hz, 1H)
MS (ESI$^-$) m/z 480 (M−1)

Example 6

Preparation of 6-benzyloxy-7-[5-(4-chloro-benzyl)-thiazol-2-yl]-2-methyl-thiazolo[3,2-a]pyrimidin-5-one

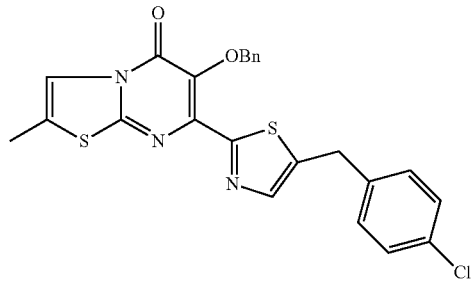 [SMILES: Cc1cn2c(=O)c(OCc3ccccc3)c(-c3ncc(Cc4ccc(Cl)cc4)s3)nc2s1]

Adapted from example 3 using the product of example 5
$^1$H NMR (300 MHz, DMSO-d$^6$) 2.44 (d, J=1.5 Hz, 3H), 4.26 (s, 2H), 5.18 (s, 2H), 7.30-7.36 (m, 5H), 7.41 (d, J=8.8 Hz, 2H), 7.45-7.53 (m, 2H), 7.87-7.92 (m, 2H)
MS (ESI$^+$) m/z 502 (M+23)

Example 7

Preparation of 7-[5-(4-chloro-benzyl)-thiazol-2-yl]-6-hydroxy-2-methyl-thiazolo[3,2-a]pyrimidin-5-one

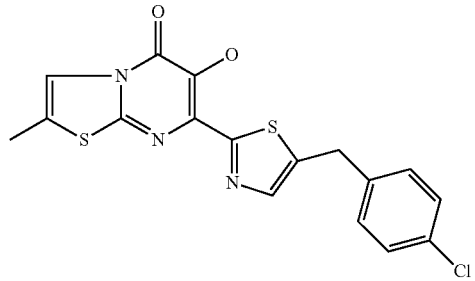 [SMILES: Cc1cn2c(=O)c(O)c(-c3ncc(Cc4ccc(Cl)cc4)s3)nc2s1]

Adapted from example 4 using the product of example 6.
$^1$H NMR (300 MHz, DMSO-d$^6$) 2.40 (d, J=1.5 Hz, 3H), 4.30 (s, 2H), 7.33-7.44 (m, 4H), 7.82 (q, J=1.5 Hz, 1H), 7.92 (t, J=0.8 Hz, 1H), 11.33 (s, 1H)
MS (ESI$^+$) m/z 390 (M+1)
HPLC 93.3%

Example 8

Preparation of 6-benzyloxy-2-methyl-5-oxo-5H-thiazolo[3,2-a]pyrimidine-7-carboxylic acid [3-(3,4-dichloro-phenyl)-2-oxo-propyl]-amide

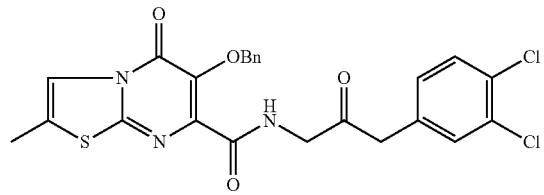 [SMILES: Cc1cn2c(=O)c(OCc3ccccc3)c(C(=O)NCC(=O)Cc3ccc(Cl)c(Cl)c3)nc2s1]

Adapted from example 2 using the product of example 1 and 1-amino-3-(3,4-dichloro-phenyl)-propan-2-one hydrochloride.
$^1$H NMR (300 MHz, DMSO-d$^6$) 2.45 (d, J=1.4 Hz, 3H), 3.89 (s, 2H), 4.20 (d, J=5.6 Hz, 2H), 5.09 (s, 2H), 7.18 (dd, J=2.1, 8.1 Hz, 1H), 7.28-7.38 (m, 3H), 7.44-7.52 (m, 3H), 7.57 (d, J=8.3 Hz, 1H), 7.93 (q, J=1.5 Hz, 1H), 8.77 (t, J=5.6 Hz, 1H).
MS (ESI$^-$) m/z 514 (M−1)

Example 9

Preparation of 6-benzyloxy-7-[5-(3,4-dichloro-benzyl)-thiazol-2-yl]-2-methyl-thiazolo[3,2-a]pyrimidin-5-one

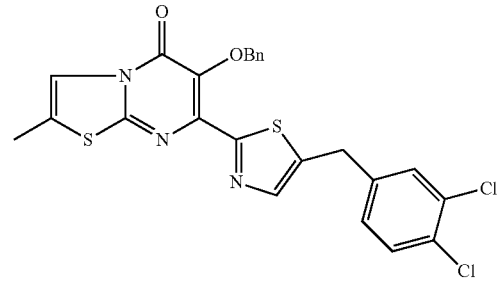 [SMILES: Cc1cn2c(=O)c(OCc3ccccc3)c(-c3ncc(Cc4ccc(Cl)c(Cl)c4)s3)nc2s1]

Adapted from example 3 using the product of example 8
$^1$H NMR (300 MHz, DMSO-d$^6$) 2.44 (d, J=1.5 Hz, 3H), 4.28 (s, 2H), 5.18 (s, 2H), 7.27-7.37 (m, 4H), 7.45-7.51 (m, 2H), 7.59-7.63 (m, 2H), 7.89 (q, J=1.4 Hz, 1H), 7.90 (t, J=0.8 Hz, 1H).
MS (ESI$^+$) m/z 536 (M+23)

Example 10

Preparation of 7-[5-(3,4-dichloro-benzyl)-thiazol-2-yl]-6-hydroxy-2-methyl-thiazolo[3,2-a]pyrimidin-5-one

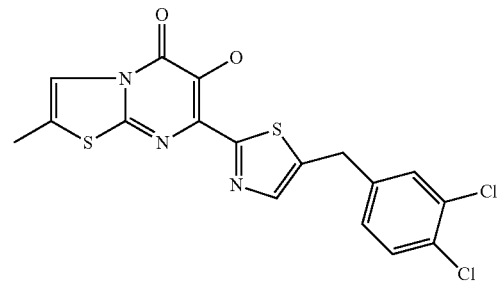 [SMILES: Cc1cn2c(=O)c(O)c(-c3ncc(Cc4ccc(Cl)c(Cl)c4)s3)nc2s1]

Adapted from example 4 using the product of example 9

$^1$H NMR (300 MHz, DMSO-d$^6$) 2.41 (d, J=1.5 Hz, 3H), 4.33 (s, 2H), 7.35 (dd, J=1.9, 8.2 Hz, 1H), 7.61 (d, J=8.2 Hz, 1H), 7.66 (d, J=1.9 Hz, 1H), 7.82 (q, J=1.4 Hz, 1H), 7.95 (s, 1H), 11.32 (s, 1H)

MS (ESI$^+$) m/z 424 (M+1)

HPLC 95.1%

Example 11

Preparation of 6-benzyloxy-7-[5-(4-chloro-3-fluoro-benzyl)-thiazol-2-yl]-2-methyl-thiazolo[3,2-a]pyrimidin-5-one

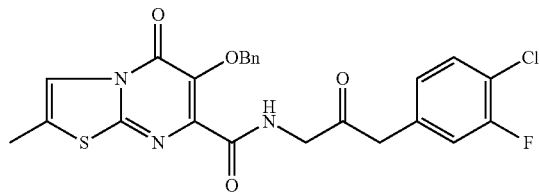

Adapted from example 2 using the product of example 1 and example 18.

$^1$H NMR (300 MHz, DMSO-d$^6$) 2.45 (d, J=1.5 Hz, 3H), 3.89 (s, 2H), 4.20 (d, J=5.8 Hz, 2H), 5.09 (s, 2H), 7.06 (dd, J=1.3, 8.3 Hz, 1H), 7.25 (dd, J=1.9, 10.5 Hz, 1H), 7.29-7.39 (m, 3H), 7.44-7.56 (m, 3H), 7.93 (q, J=1.6 Hz, 1H), 8.78 (t, J=5.6 Hz, 1H).

MS (ESI$^-$) m/z 498 (M−1)

Example 12

Preparation of 6-benzyloxy-2-methyl-5-oxo-5H-thiazolo[3,2-a]pyrimidine-7-carboxylic acid [3-(4-chloro-3-fluoro-phenyl)-2-oxo-propyl]-amide

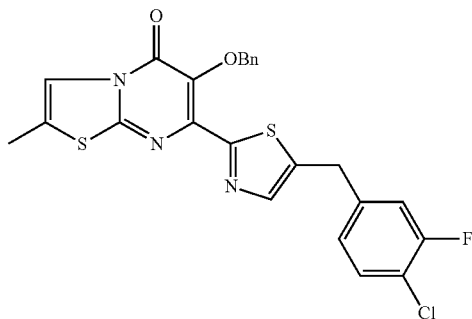 [SMILES: Cc1cn2c(=O)c(OCc3ccccc3)c(-c3ncc(Cc4ccc(Cl)c(F)c4)s3)nc2s1]

Adapted from example 3 using the product of example 11

$^1$H NMR (300 MHz, DMSO-d$^6$) 2.44 (d, J=1.3 Hz, 3H), 4.29 (s, 2H), 5.19 (s, 2H), 7.18 (dd, J=1.6, 8.4 Hz, 1H), 7.30-7.36 (m, 3H), 7.40 (dd, J=1.8, 10.4 Hz, 1H), 7.45-7.51 (m, 2H), 7.56 (t, J=8.1 Hz, 1H), 7.87-7.92 (m, 2H)

MS (ESI$^+$) m/z 520 (M+23)

Example 13

Preparation of 7-[5-(4-chloro-3-fluoro-benzyl)-thiazol-2-yl]-6-hydroxy-2-methyl-thiazolo[3,2-a]pyrimidin-5-one

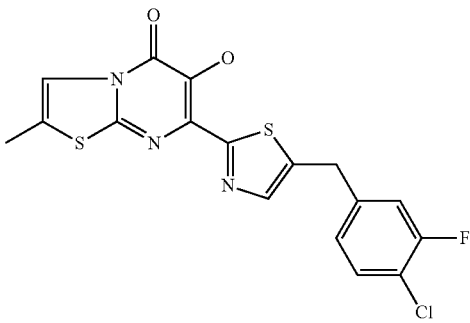 [SMILES: Cc1cn2c(=O)c(O)c(-c3ncc(Cc4ccc(Cl)c(F)c4)s3)nc2s1]

Adapted from example 4 using the product of example 12

$^1$H NMR (300 MHz, DMSO-d$^6$) 2.41 (d, J=1.5 Hz, 3H), 4.33 (s, 2H), 7.22 (dd, J=1.9, 8.0 Hz, 1H), 7.44 (dd, J=2.0, 10.6 Hz, 1H), 7.57 (t, J=8.1 Hz, 1H), 7.82 (q, J=1.5 Hz, 1H), 7.95 (s, 1H), 11.33 (s, 1H).

MS (ESI$^+$) m/z 430 (M+23)

HPLC 94.6%

Example 14

Preparation of (4-chloro-3-fluoro-phenyl)-acetonitrile

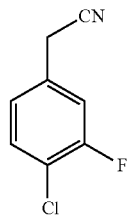

To a boiling solution of 4-chloro-3-flurorobenzyl bromide (10 g, 44.8 mmol) in absolute ethanol (40 ml) was added a solution of potassium cyanide (2.9 g, 44.8 mmol) in water (6 ml). The mixture was refluxed for 1.5 hours, then most of the ethanol was distilled off under reduced pressure and the cooled residue poured into water. The solution was extracted three times with ether. The combined organic layers were washed with brine, dried and concentrated into dryness to give the titled product (7.8 g, 93% yield)

$^1$H NMR (300 MHz, DMSO-d$^6$) 4.09 (s, 2H), 7.25 (ddd, J=0.8, 2.0, 8.2 Hz, 1H), 7.43 (dd, J=2.0, 10.0 Hz, 1H), 7.64 (t, J=8.2 Hz, 1H).

MS (ESI$^-$) m/z 168 (M−1)

Example 15

Preparation of (4-chloro-3-fluoro-phenyl)-acetic acid

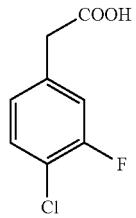 [SMILES: O=C(O)Cc1ccc(Cl)c(F)c1]

A mixture of the product of example 14 (7.8 g, 0.046 mol), water (7.5 ml), concentrated sulfuric acid (7.5 ml) and acetic acid (7.5 ml) was heated at reflux for 2 hours. After being cooled to room temperature, the mixture was poured into ice-water. The resulting solids were collected by filtration and washed by diethyl ether to give the titled product (6.8 g, 79%)

$^1$H NMR (300 MHz, DMSO-d$^6$) 3.64 (s, 2H), 7.14 (ddd, J=0.6, 2.1, 8.2 Hz, 1H), 7.34 (dd, J=2.1, 10.6 Hz, 1H), 7.52 (t, J=8.1 Hz, 1H).

MS (ESI$^-$) m/z 187 (M−1)

Example 16

Preparation of (4-chloro-3-fluoro-phenyl)-acetyl chloride

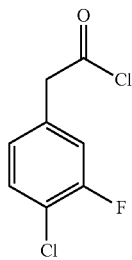

A mixture of the product of example 15 (4.9 g, 26 mmol) with thionyl chloride (50 ml) was refluxed for 3 hours. Then thionyl chloride was removed under reduced pressure. The residue was redistilled under reduced pressure to give crude titled acyl chloride, which was used directly in the next step reaction. (3.2 g, 60% yield)

Example 17

Preparation of 5-(4-chloro-3-fluoro-benzyl)-oxazole-4-carboxylic acid ethyl ester

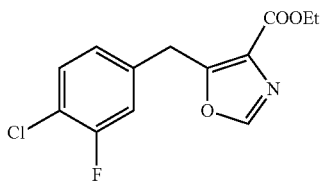 [SMILES: CCOC(=O)c1ncoc1Cc1ccc(Cl)c(F)c1]

To a solution of potassium tert-butoxide (3.5 g, 31.25 mmol) in THF (50 ml) was added ethyl isocyanoacetate (3.5 g, 31.25 mmol) dropwise at 5° C. After stirring for 45 minutes, the product of example 16 (3.2 g, 15.5 mmol) was added dropwise. Then the mixture was stirred overnight at room temperature. The reaction mixture was filtered and the filtrate was concentrated. The residue was purified by column chromatography (PE/EA=5/1) to give the titled compound (2.5 g, 67.7 yield)

$^1$H NMR (300 MHz, DMSO-d$^6$) 1.29 (t, J=7.1 Hz, 3H), 4.30 (q, J=7.1 Hz, 2H), 4.41 (s, 2H), 7.11 (ddd, J=0.6, 2.1, 8.3 Hz, 1H), 7.34 (dd, J=2.0, 10.4 Hz, 1H), 7.54 (t, J=8.1 Hz, 1H), 8.40 (s, 1H).

MS (ESI$^+$) m/z 306 (M+23)

Example 18

Preparation of 1-amino-3-(4-chloro-3-fluoro-phenyl)-propan-2-one hydrochloride

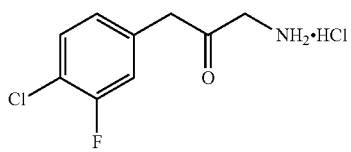

A mixture of the product of example 17 (2.5 g, 10.53 mmol) with hydrochloride acid (6 mol/l, 30 ml) was refluxed for about 3 hours and then cooled to room temperature. The solids were collected by filtration, washed with EA and dried to give the titled product (1.7 g, 81%)

$^1$H NMR (300 MHz, DMSO-d$^6$) 3.96 (s, 2H), 4.03 (s, 2H), 7.10 (dd, J=1.9, 8.2 Hz, 1H), 7.29 (d, J=1.9, 10.4 Hz, 1H), 7.56 (t, J=8.1 Hz, 1H), 8.15-8.42 (brs, 3H).

MS (ES$^+$) m/z 202 (M+1)

Example 19

Preparation of 5-fluoro-2,N,N-trimethyl-benzenesulfonamide

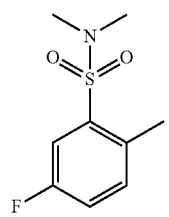

A mixture of 5-fluoro-2-methylbenzene sulfonylchloride (2.1 mL, 14.3 mmol) in THF (18 mL) and 2 M dimethylamine in methanol (18 mL), was stirred at room temperature for 0.5 h. The resulting mixture was concentrated under reduced pressure to give a crude product as a mixture of white solid and colourless oil. The crude product was purified by column (30% EtOAc in Hexane) to give the titled compound as a colourless oil (3.09 g, 99% yield).

Example 20

Preparation of 2-bromomethyl-5-fluoro-N,N-dimethyl-benzenesulfonamide

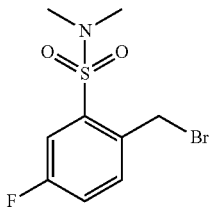

To a solution of the product of example 19 (3 g, 13.8 mmol) in DCE (40 mL), was added n-bromosuccinamide (2.8 g, 15.19 mmol) and stirred at 80° C. for 5 min before AIBN (300 mg, 0.016 mmol) was added and heated at 80° C. for 5 h (95% conversion). The reaction mixture was concentrated under reduced pressure to give a crude product as a yellow solid. The crude product was purified by column (10-20% ethylacetate in hexane) to give the titled product. (50% yield)

MS (ESI$^+$) m/z 296, 298 Br [M+H$^+$]

Example 21

Preparation of 2-cyanomethyl-5-fluoro-N,N-dimethyl-benzenesulfonamide

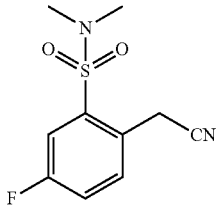

A mixture of the product of example 20 (~90% pure, 729 mg, 2.46 mmol) in a mixture of DMF:H$_2$O (3 mL:2 mL) and sodium cyanide (362 mg, 7.4 mmol) was stirred at room temperature overnight. The resulting mixture was quenched with saturated NaHCO$_3$ (12 mL) and extracted with ethylacetate (3×30 mL). The extracts were combined and washed with saturated NaCl (2×30 mL) and water (2×30 mL). The organic layer was separated, dried over anhydrous MgSO$_4$ and concentrated under reduced pressure to give the titled product as a colourless oil (503 mg, 85% yield).

$^1$H NMR CDCl$_3$, 300 MHz: δ 2.86 (s, 6H, —N(CH$_3$)$_2$), 4.19 (s, 2H, —CH$_2$C≡N), 7.35 (m, 1H, ArH), 7.69 (m, 2H, ArH).

MS (ESI$^+$) m/z 243 [M+H$^+$], 265 [M+Na$^+$]

Example 22

Preparation of (2-dimethylsulfamoyl-4-fluoro-phenyl)-acetic acid

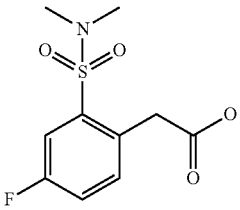

A solution of the product of example 33 (300 mg, 1.24 mmol) in 4M HCl in dioxane (14 mL) was heated at 40° C. for 2 h. The reaction mixture was concentrated under reduced pressure to give the title compound as a yellow oil and was used without further purification.

MS (ESI$^+$) m/z 261 [M$^+$]

Example 23

Preparation of 1-chloro-3-(4-fluoro-phenyl)-propan-2-one

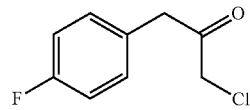 [SMILES: O=C(CCl)Cc1ccc(F)cc1]

1. To a chilled (0° C.) solution of 4-fluoro-phenylacetyl chloride (14.07 mmol, 2.43 g) in diethylether (15 mL), was added a cold solution of freshly distilled diazomethane in diethylether (16 mmol) and stirred at 0° C. for 15 min and then at room temperature for 15 min. The resulting mixture of diazoketone was used in the next step without further purification (confirmed by mass spec).

2. One third of the above diazoketone solution (in diethyl ether) was cooled to −30° C. and 4M HCl in dioxane (3 mL) was added and stirred at −30° C. for 0.5 h and then at room temperature for 0.5 h. The reaction mixture was quenched with water (20 mL) and extracted with ethyl acetate (30 mL). The organic layer was separated and dried over anhydrous MgSO$_4$ and concentrated under reduced pressure to give a crude product as slightly yellow oil. The crude product was purified by column chromatography (15-20% EtOAc in hexane) to give the titled compound with R$_f$=0.016 (200 mg, 19% yield)

$^1$H NMR: CDCl$_3$, 300 MHz: δ 3.88 (s, 2H, —CH$_2$Cl), 4.11 (s, 2H, —CH$_2$(C═O)), 7.04 (t, J=8.7 Hz, 2H, ArH), 7.20 (t, dd=4.8, 8.8 Hz, 2H, ArH).

Example 24

Preparation of 2-[3-(4-fluoro-phenyl)-2-oxo-propyl]-isoindole-1,3-dione

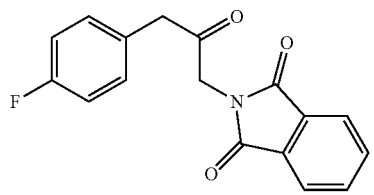 [SMILES: O=C(Cc1ccc(F)cc1)CN1C(=O)c2ccccc2C1=O]

To a solution of the product of example 23 (85 mg, 0.45 mmol) in DMF (1 mL), under a nitrogen atmosphere, was added potassium salt of phthalamide (96 mg, 0.52 mmol). The resulting mixture was stirred at room temperature for 1 h. The reaction mixture was quenched with a mixture of ice-water and filtered. The slightly pink solid was washed with water to give the titled compound as a white product (79 mg, 62% yield).

$^1$H NMR CDCl$_3$, 300 MHz: δ 3.82 (s, 2H, —CH$_2$N—), 4.51 (s, 2H, —CH$_2$(C═O)), 7.04 (m, 2H, ArHF), 7.23 (m, 2H, ArHF), 7.74 (m, 2H, ArH), 7.86 (m, 2H, ArH).

MS (ESI$^+$) m/z 298 [M+H$^+$]

3. BIOLOGICAL EXAMPLES

Activity of Selected Examples Against Wild Type and Mutant Integrases and HIV-s

PhenoScreen Assay

Monogram Bioscience' PhenoScreen assay allows the evaluation of integrase inhibitors for activity against a variety of HIV variants. The assay uses virus generated from 2 DNA constructs; one containing the HIV LTR, gag and pol regions, as well as a luciferase reporter gene in place of the viral envelope genes, and a second DNA construct containing the amphotrophic murine leukemia virus (A-MLV) envelope gene required to pseudotype virions and render them capable of entry into a target cell. Viruses generated using these constructs by transfection into a producer cell line such as 293T are capable of one-round of infection only. Successful integration events are directly proportional to the levels of luciferase expression 48 h after infection.

The viral variants chosen by Avexa Ltd to screen their in-house integration inhibitors against consist of mutations within the viral integrase enzyme known to confer resistance to a number of known integration inhibitors published in the literature. In particular, the viral variants containing the Q148H/G140S double mutation in integrase, and the N155H/E92Q double mutation in integrase, represent two of the more common viruses identified to arise in patients that are failing treatment with Isentress (Raltegravir, MK-0518).

In-House IN-Screen Assay

Similar to the PhenoScreen assay, Avexa's IN-Screen assay relies on reporter gene expression levels 58 h following infection. However, in contrast to the PhenoScreen assay developed at Monogram Biosciences, Avexa's assay uses full-length, replication competent HIV generated by transfection of 293T cells, and target cells stably transfected with a construct containing B-galactosidase under the control of a TAT-dependent HIV LTR promoter. Upon virus infection (at a multiplicity of infection of 0.1) and successful integration, the viral Tat protein is produced from the newly integrated provirus which is then able to trans-activate expression of the B-galactosidase reporter gene. B-galactosidase expression is then measured in the cell population using the commercially available GalactoStar kit (Applied Biosystems) according to the manufacturers instructions.

Mutant Enzymes:

HIV integrase was mutated within a shuttle vector (pGEM) containing the majority of the HIV-1 gag and pol sequence using site directed mutagenesis to generate integrase sequences that have been published as conferring resistance to published integrase inhibitors. These include, but are not limited to, mutations such as Q148K. The integrase coding region was then subject to PCR and cloned into a bacterial expression vector. The specific introduction of desired mutation(s) was confirmed by sequence analysis. Proteins were expressed, purified and used in strand transfer assays.

Strand Transfer Assay (Enzyme Assay):

A strand transfer assay procedure similar to that published (Ovenden et al. Phytochemistry. 2004 December; 65(24): 3255-9.) is used. Briefly, 400 ng of the enzyme, wild type or drug resistant mutant, is mixed with the compound to be tested and incubated with 30 nM substrate DNA. The substrate DNA is designed to mimic HIV DNA termini that has undergone 3'end processing, and consists of the annealed U5 LTR sequence oligonucleotides tagged with Digoxigenin (DIG; 5'-ACTGCTAGAGATTTTCCACACTGAC-TAAAAGGGTC-DIG-3') or biotin (5'-Bio-GACCCTTT-TAGTCAGTGTGGAAAATCTCTAGCA-3') so that each substrate has either a DIG or Bio tag on opposite strands. Reactions are carried out for 1 hr at 37° C. Products generated as a result of strand transfer activity are bound to streptavidin plates and detected using anti-DIG-alkaline phosphatase conjugate and p-nitro phenyl phosphate substrate.

Both the Phenosense assay and the Enzyme assay give substantially the same activity values for any particular compound and enzyme pair. The activity of one compound in one assay can therefore be directly compared to the activity of a second compound in the other assay.

TABLE 1

Activity of selected examples against wild type and mutant integrases and HIV-s

| Compound | Phenosense assay | | | | | | Enzyme | | |
| --- | --- | --- | --- | --- | --- | --- | --- | --- | --- |
| | WT | Y143R | E92Q N155H | G140S Q148H | T125K F121Y | T661 S153Y | WT | E92Q/N 155H | G140S/ Q148H |
| | | | | | | | +++ | ++ | +++ |

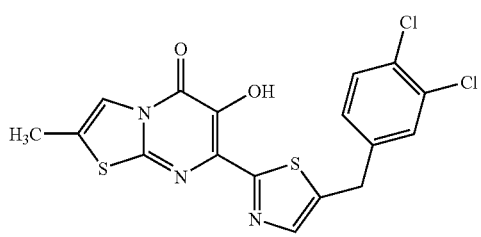

Example 10

TABLE 1-continued

Activity of selected examples against wild type and mutant integrases and HIV-s

| Compound | Phenosense assay | | | | | Enzyme | | |
|---|---|---|---|---|---|---|---|---|
| | WT | Y143R | E92Q N155H | G140S Q148H | T125K F121Y | T661 S153Y | WT | E92Q/N 155H | G140S/ Q148H |

Example 13: +++ ++ ++

Example 4: ++++ +++ ++++

Example 7: +++ ++ +

Comparative Example 1ᵃ: +++

Comparative Example 2b: ++

TABLE 1-continued

Activity of selected examples against wild type and mutant integrases and HIV-s

| Compound | Phenosense assay | | | | | | Enzyme | | |
|---|---|---|---|---|---|---|---|---|---|
| | WT | Y143R | E92Q N155H | G140S Q148H | T125K F121Y | T66I S153Y | WT | E92Q/N 155H | G140S/ Q148H |
| 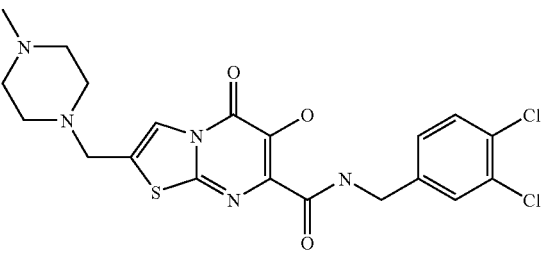 Comparative Example 3c | +++ | +++ | + | + | + | ++ | +++ | | |
| 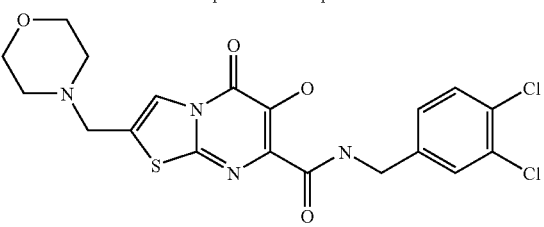 Comparative Example 4d | +++ | +++ | + | + | + | + | +++ | | |
| 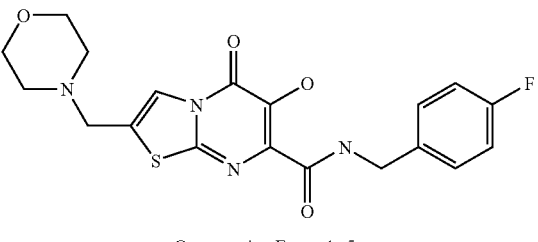 Comparative Example 5e | ++ | ++ | + | + | + | + | ++ | | |
| 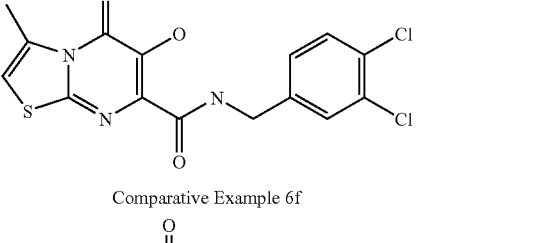 Comparative Example 6f | +++ | +++ | + | + | + | + | +++ | | |
| Comparative Example 7g | +++ | +++ | + | + | + | ++ | +++ | | |

+++ indicates value between 0.001 μM and 1 μM
++ indicates value between 1 μM and 10 μM
+indicates value greater than 10 μM
aExample 17.4 of International Patent Application No. PCT/AU2007/001980
bExample 17.3 of International Patent Application No. PCT/AU2007/001980
cExample 17.7.6 of International Patent Application No. PCT/AU2007/001980
dExample 17.7.2 of International Patent Application No. PCT/AU2007/001980
eExample 17.7.1 of International Patent Application No. PCT/AU2007/001980
fExample 17.5 of International Patent Application No. PCT/AU2007/001980
gExample 17.6 of International Patent Application No. PCT/AU2007/001980

The results above indicate that the compounds of the present invention have superior activity profiles against mutant HIV integrases than analogues in International Patent Application No. PCT/AU2007/001980 in the name of Avexa. Ltd which are not of the present invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of Formula I or a pharmaceutically acceptable salt thereof wherein:

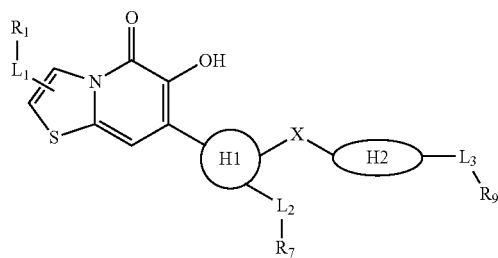

$L_1$-$R_1$ is 0-2 substituents wherein:
  each $L_1$ is independently absent or is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, NH;
  each $R_1$ is independently selected from the group consisting of hydrogen, $C_{1-10}$alkyl wherein one or more of the carbon atoms of the alkyl chain may optionally be replaced with oxygen atoms, $C_{1-10}$alkylNR$_3$R$_4$, halo, NR$_3$R$_4$, alkylaryl, S(O)N$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms;
  $R_3$ and $R_4$ are each independently selected from the group consisting of hydrogen, $C_{1-10}$alkyl, $C_{1-10}$NR$_5$R$_6$, —(CO)(CO)NR$_5$R$_6$; or $R_3$ and $R_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, $C_{1-4}$alkyl, $CO_2C_{1-4}$alkyl, NR$_5$R$_6$; $C_{1-4}$-alkylNR$_5$R$_6$;
  $R_5$ and $R_6$ are each independently selected from the group consisting of H and $C_{1-4}$alkyl or $R_5$ and $R_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and $C_{1-4}$alkyl;
  when $R_1$ is alkylaryl, the aryl group of said alkylaryl substituent is optionally substituted with a substituent selected from $C_{1-10}$alkyl, —O—$C_{1-10}$alkyl, $C_{1-10}$alkylNR$_3$R$_4$, —O—$C_{1-10}$alkylNR$_3$R$_4$, halo, NR$_3$R$_4$, alkylaryl, —O-alkylaryl, SO$_2$NR$_3$R$_4$ $H_1$ is a 5- or 6-membered saturated, partially saturated or aromatic ring containing between 1 and 4 heteroatoms independently selected from the group consisting of N, O and S;

$L_2$-$R_7$ is 0-2 substituents wherein:
  each $L_2$ is independently absent or is group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
  each $R_7$ is independently selected from the group consisting of hydrogen, $C_{1-10}$alkyl wherein one or more of the carbon atoms of the alkyl chain may optionally be replaced with oxygen atoms, $C_{1-10}$alkylNR$_3$R$_4$, halo, NR$_3$R$_4$, alkylaryl, S(O)N$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms;

X is CR$_8$R$_{8'}$;
  each of R$_8$ and R$_{8'}$ is independently selected from the group consisting of H and CH$_3$, preferably H;

$H_2$ is a 5- or 6-membered saturated, partially saturated or aromatic ring containing between 0 and 4 heteroatoms independently selected from the group consisting of N, O and S;

$L_3$-$R_9$ is 0-3 substituents wherein:
  each $L_3$ is independently absent or is group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
  each $R_9$ is independently selected from the group consisting of hydrogen, $C_{1-10}$alkyl wherein one or more of the carbon atoms of the alkyl chain may optionally be replaced with oxygen atoms, $C_{1-10}$alkylNR$_3$R$_4$, halo, NR$_3$R$_4$, heterocyclyl, heteroaryl, alkylaryl, S(O)N$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms.

2. A compound according to claim 1 wherein $L_1$ is —CH$_2$— and $R_1$ is N-piperidine, N-piperazine, N,N'-methylpiperazine, or N-morpholino.

3. A compound according to claim 1 wherein $H_1$ is a five membered aromatic heterocycle selected from the group consisting of thiazole, oxazole, oxadiazole, imidazole, triazole, tetrazole, and thiazole.

4. A compound according to claim 1 wherein $H_1$ is 2,5-substituted thiazole.

5. A compound according to claim 1 wherein $H_2$ is phenyl.

6. A compound according to claim 1 wherein $L_3$-$R_9$ is at least 2 substituents wherein the first $L_3$-$R_9$ is halo and in the second $L_3$-$R_9$, $L_3$ is absent or is selected from >C=O and $R_9$ is selected from the group consisting of halo, $NR_3R_4$ and $SO_2NR_3R_4$.

7. A compound according to claim 1 wherein $NR_3R_4$, where it occurs in $L_3$-$R_9$, is morpholino, a five-membered cyclic sulphonamide (such as isothiazolidine) or a six membered cyclic sulphonamide.

8. A compound according to claim 1 wherein $L_3$-$R_9$ is one substituent and is halo.

9. A compound according to claim 1 selected from the group consisting of:

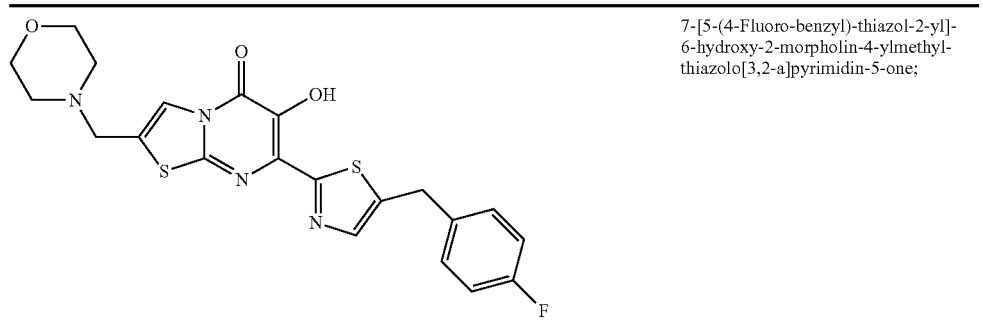

7-[5-(4-Fluoro-benzyl)-thiazol-2-yl]-6-hydroxy-2-morpholin-4-ylmethyl-thiazolo[3,2-a]pyrimidin-5-one;

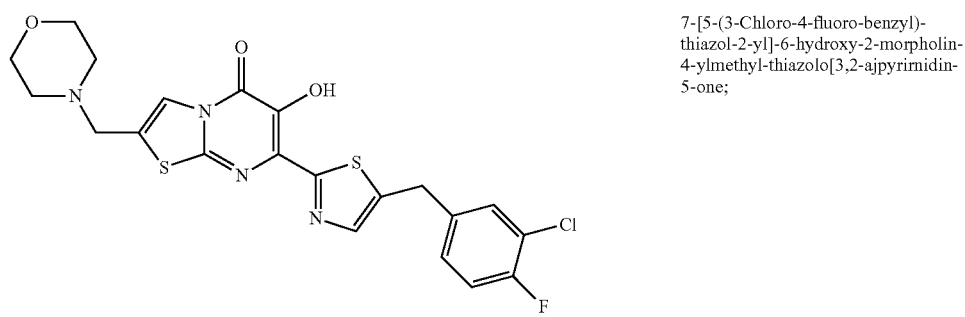

7-[5-(3-Chloro-4-fluoro-benzyl)-thiazol-2-yl]-6-hydroxy-2-morpholin-4-ylmethyl-thiazolo[3,2-a]pyrimidin-5-one;

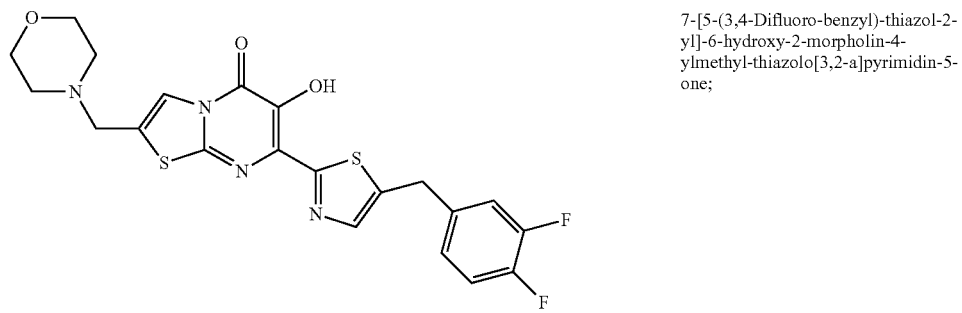

7-[5-(3,4-Difluoro-benzyl)-thiazol-2-yl]-6-hydroxy-2-morpholin-4-ylmethyl-thiazolo[3,2-a]pyrimidin-5-one;

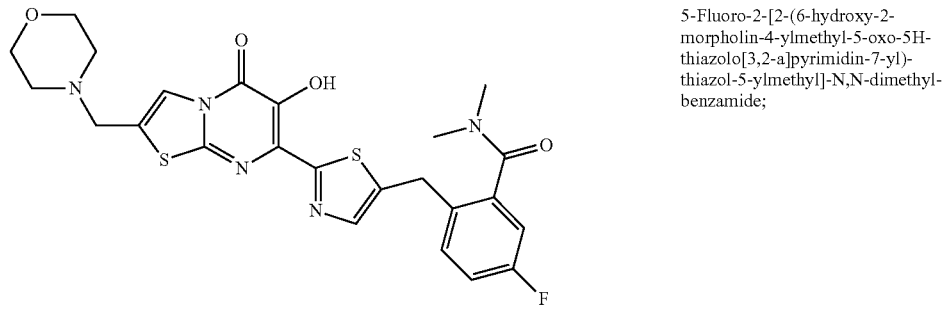

5-Fluoro-2-[2-(6-hydroxy-2-morpholin-4-ylmethyl-5-oxo-5H-thiazolo[3,2-a]pyrimidin-7-yl)-thiazol-5-ylmethyl]-N,N-dimethyl-benzamide;

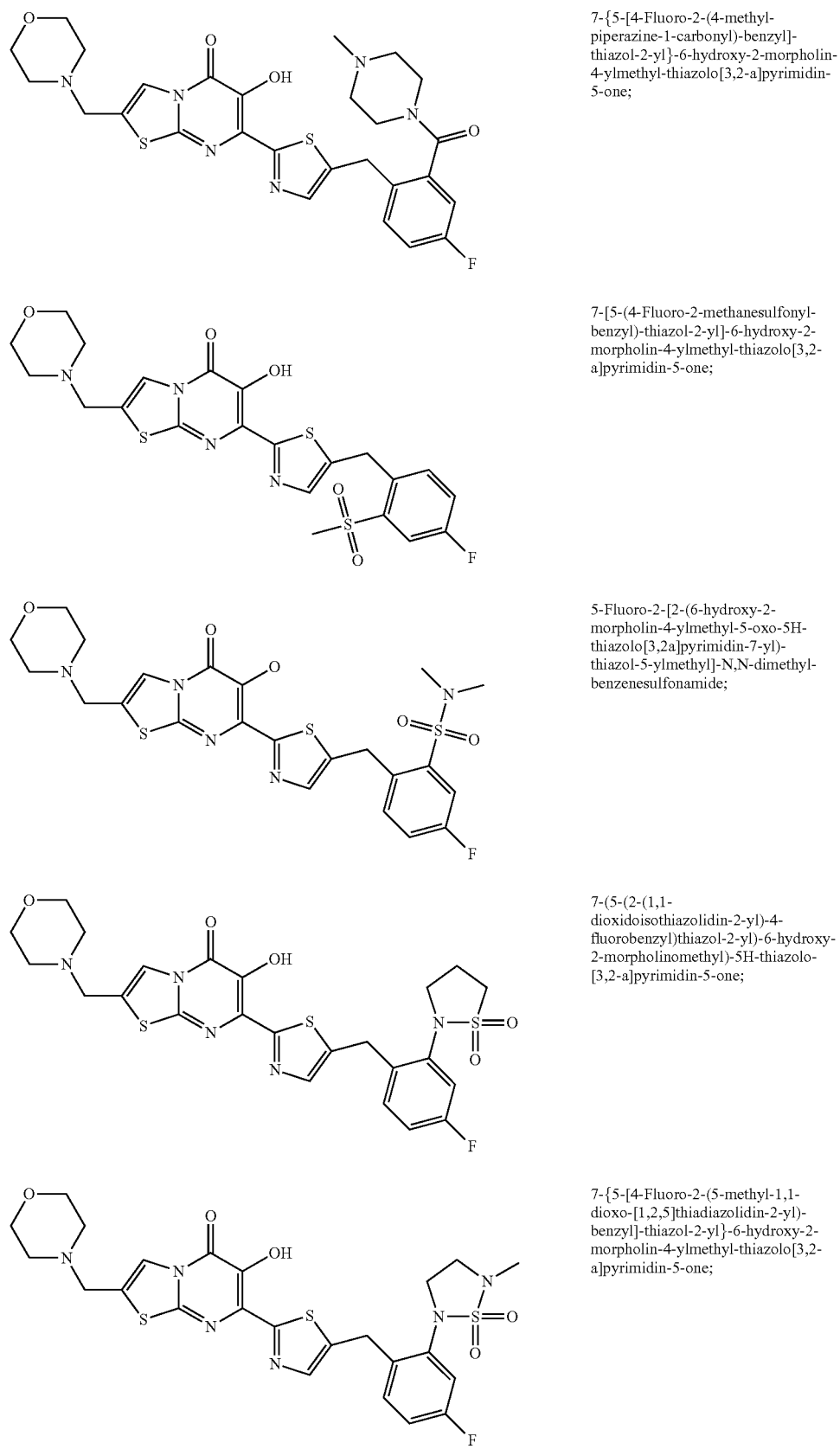

7-{5-[4-Fluoro-2-(4-methyl-piperazine-1-carbonyl)-benzyl]-thiazol-2-yl}-6-hydroxy-2-morpholin-4-ylmethyl-thiazolo[3,2-a]pyrimidin-5-one;

7-[5-(4-Fluoro-2-methanesulfonyl-benzyl)-thiazol-2-yl]-6-hydroxy-2-morpholin-4-ylmethyl-thiazolo[3,2-a]pyrimidin-5-one;

5-Fluoro-2-[2-(6-hydroxy-2-morpholin-4-ylmethyl-5-oxo-5H-thiazolo[3,2a]pyrimidin-7-yl)-thiazol-5-ylmethyl]-N,N-dimethyl-benzenesulfonamide;

7-(5-(2-(1,1-dioxidoisothiazolidin-2-yl)-4-fluorobenzyl)thiazol-2-yl)-6-hydroxy-2-morpholinomethyl)-5H-thiazolo-[3,2-a]pyrimidin-5-one;

7-{5-[4-Fluoro-2-(5-methyl-1,1-dioxo-[1,2,5]thiadiazolidin-2-yl)-benzyl]-thiazol-2-yl}-6-hydroxy-2-morpholin-4-ylmethyl-thiazolo[3,2-a]pyrimidin-5-one;

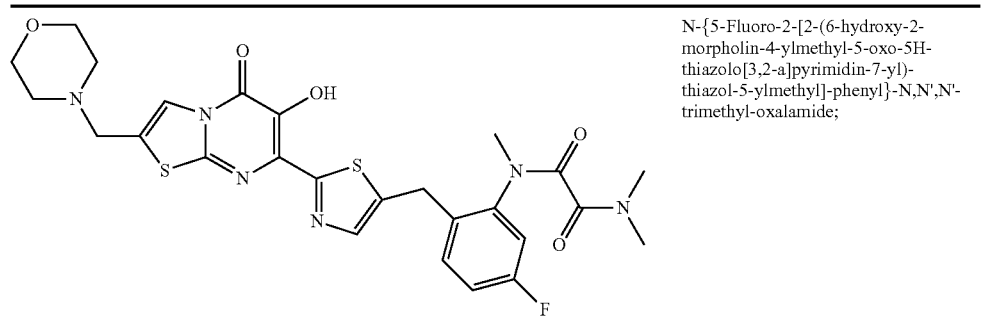

N-{5-Fluoro-2-[2-(6-hydroxy-2-morpholin-4-ylmethyl-5-oxo-5H-thiazolo[3,2-a]pyrimidin-7-yl)-thiazol-5-ylmethyl]-phenyl}-N,N',N'-trimethyl-oxalamide;

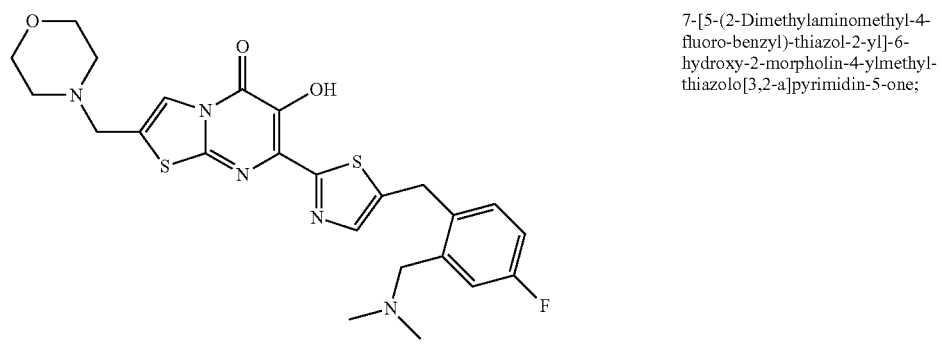

7-[5-(2-Dimethylaminomethyl-4-fluoro-benzyl)-thiazol-2-yl]-6-hydroxy-2-morpholin-4-ylmethyl-thiazolo[3,2-a]pyrimidin-5-one;

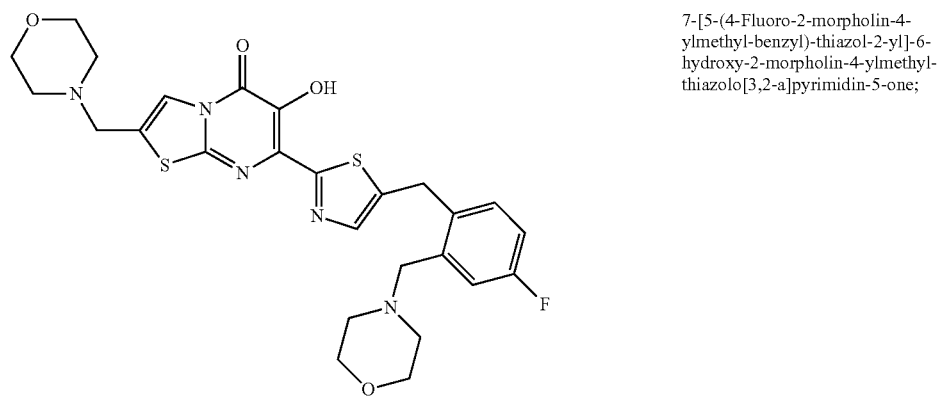

7-[5-(4-Fluoro-2-morpholin-4-ylmethyl-benzyl)-thiazol-2-yl]-6-hydroxy-2-morpholin-4-ylmethyl-thiazolo[3,2-a]pyrimidin-5-one;

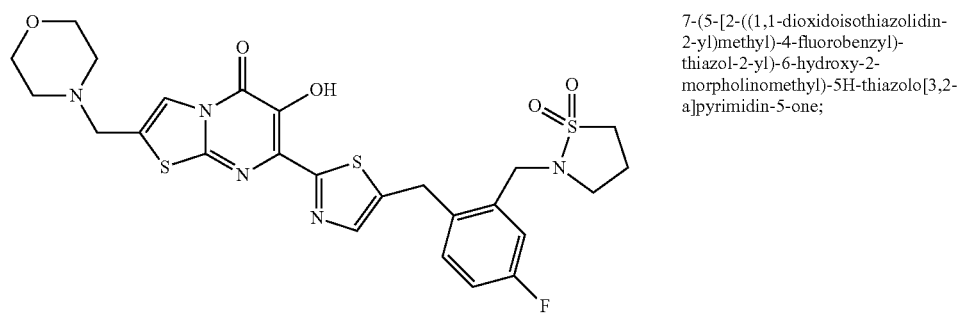

7-(5-[2-((1,1-dioxidoisothiazolidin-2-yl)methyl)-4-fluorobenzyl)-thiazol-2-yl)-6-hydroxy-2-morpholinomethyl)-5H-thiazolo[3,2-a]pyrimidin-5-one;

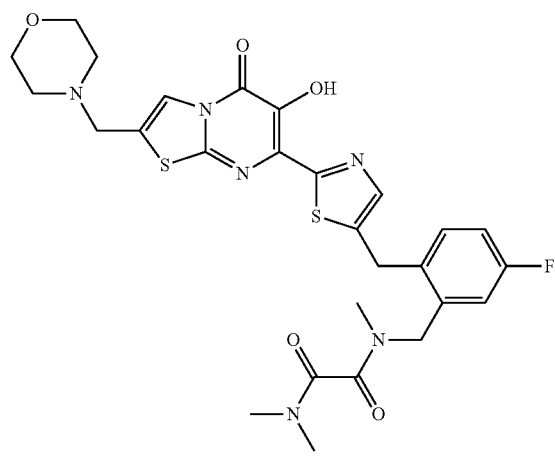 [SMILES: CN(C)C(=O)C(=O)N(C)Cc1cc(F)ccc1Cc1cnc(-c2nc3sc(CN4CCOCC4)cn3c(=O)c2O)s1]

N-{5-Fluoro-2-[2-(6-hydroxy-2-morpholin-4-ylmethyl-5-oxo-5H-thiazolo[3,2-a]pyrimidin-7-yl)-thiazol-5-ylmethyl]-benzyl}-N,N',N'-trimethyl-oxalamide;

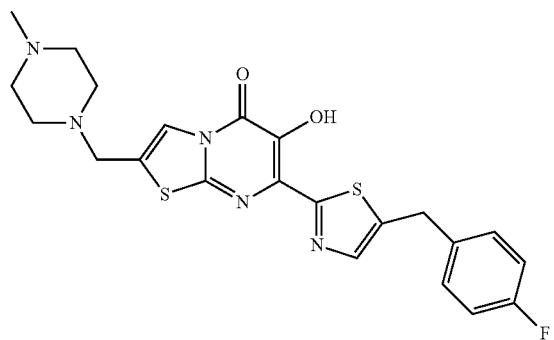 [SMILES: CN1CCN(Cc2cn3c(=O)c(O)c(-c4ncc(Cc5ccc(F)cc5)s4)nc3s2)CC1]

7-[5-(4-Fluoro-benzyl)-thiazol-2-yl]-6-hydroxy-2-(4-methyl-piperazin-1-ylmethyl)-thiazolo[3,2-a]pyrimidin-5-one;

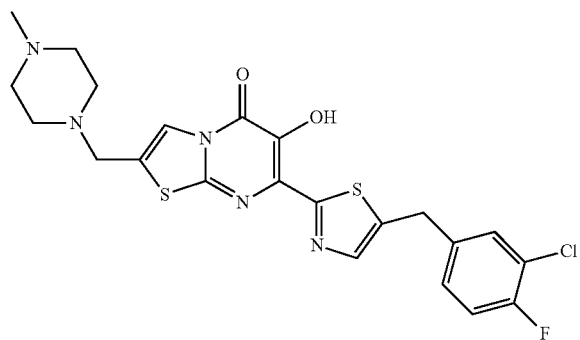 [SMILES: CN1CCN(Cc2cn3c(=O)c(O)c(-c4ncc(Cc5ccc(F)c(Cl)c5)s4)nc3s2)CC1]

7-[5-(3-Chloro-4-fluoro-benzyl)-thiazol-2-yl]-6-hydroxy-2-(4-methyl-piperazin-1-ylmethyl)-thiazolo[3,2-a]pyrimidin-5-one;

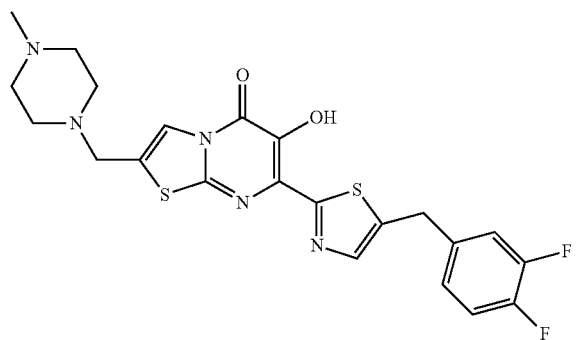 [SMILES: CN1CCN(Cc2cn3c(=O)c(O)c(-c4ncc(Cc5ccc(F)c(F)c5)s4)nc3s2)CC1]

7-[5-(3,4-Difluoro-benzyl)-thiazol-2-yl]-6-hydroxy-2-(4-methyl-piperazin-1-ylmethyl)-thiazolo[3,2-a]pyrimidin-5-one;

-continued

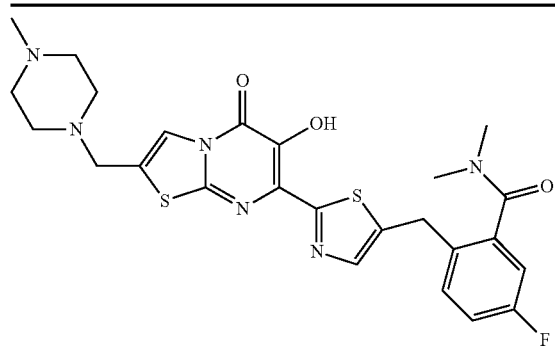

5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-N,N-dimethyl-benzamide;

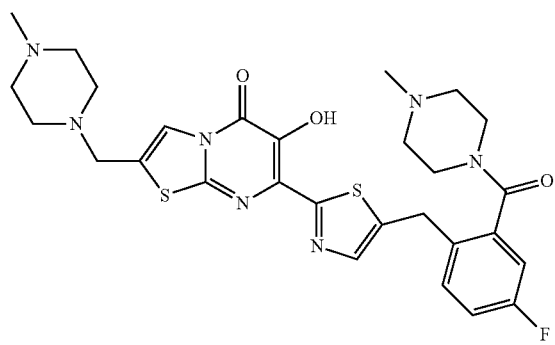 [SMILES: CN1CCN(Cc2cn3c(=O)c(O)c(-c4ncc(Cc5ccc(F)cc5C(=O)N5CCN(C)CC5)s4)nc3s2)CC1]

7-{5-[4-Fluoro-2-(4-methyl-piperazine-1-carbonyl)-benzyl]-thiazol-2-yl}-6-hydroxy-2-(4-methyl-piperazin-1-ylmethyl)-thiazolo[3,2-a]pyrimidin-5-one;

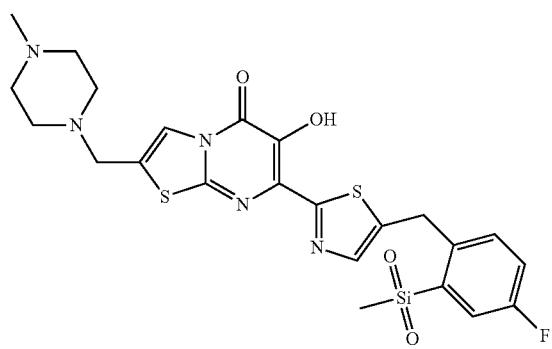

7-[5-(4-Fluoro-2-methanesulfonyl-benzyl)-thiazol-2-yl]-6-hydroxy-2-(4-methyl-piperazin-1-ylmethyl)-thiazolo[3,2-a]pyrimidin-5-one;

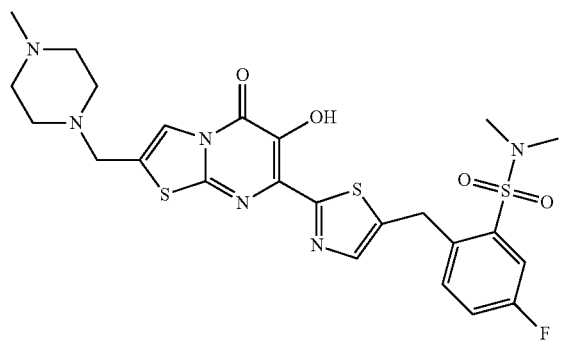 [SMILES: CN1CCN(Cc2cn3c(=O)c(O)c(-c4ncc(Cc5ccc(F)cc5S(=O)(=O)N(C)C)s4)nc3s2)CC1]

5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-N,N-dimethyl-benzenesulfonamide;

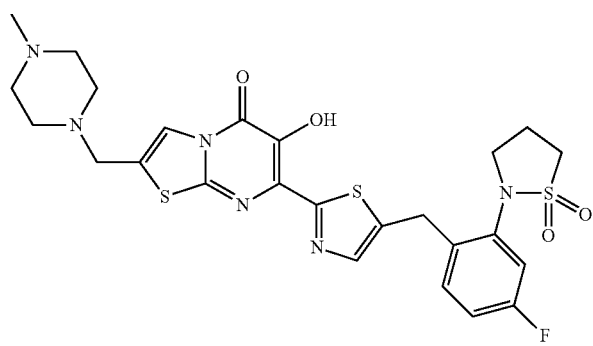 [SMILES: CN1CCN(Cc2cn3c(=O)c(O)c(-c4ncc(Cc5ccc(F)cc5N5CCCS5(=O)=O)s4)nc3s2)CC1]

7-{5-[2-(1,1-Dioxo-isothiazolidin-2-yl)-4-fluorobenzyl]-thiazol-2-yl}-6-hydroxy-2-(4-methyl-piperazin-1-ylmethyl)-thiazolo[3,2-a]pyrimidin-5-one;

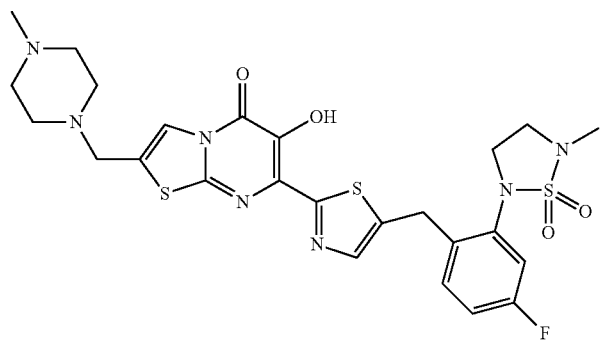 [SMILES: CN1CCN(Cc2cn3c(=O)c(O)c(-c4ncc(Cc5ccc(F)cc5N5CCN(C)S5(=O)=O)s4)nc3s2)CC1]

7-{5-{4-Fluoro-2-(5-methyl-1,1-dioxo-[1,2,5]thiadiazolidin-2-yl)-benzyl]-thiazol-2-yl}-6-hydroxy-2-(4-methyl-piperazin-1-ylmethyl)-thiazolo[3,2-a]pyrimidin-5-one;

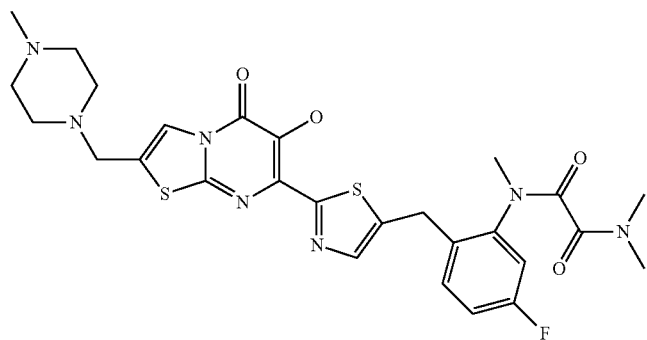 [SMILES: CN1CCN(Cc2cn3c(=O)c(O)c(-c4ncc(Cc5ccc(F)cc5N(C)C(=O)C(=O)N(C)C)s4)nc3s2)CC1]

N-(5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-phenyl)-N,N',N'-trimethyl-oxalamide;

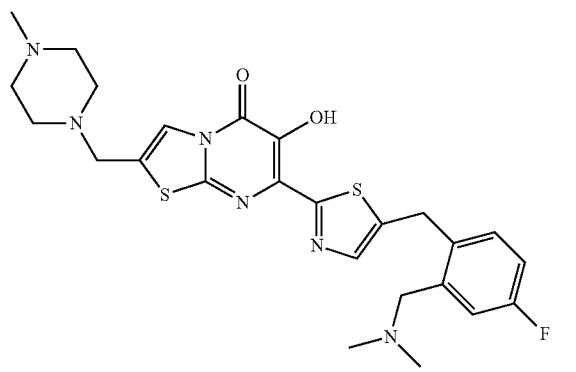 [SMILES: CN(C)Cc1cc(F)ccc1Cc1cnc(-c2nc3sc(CN4CCN(C)CC4)cn3c(=O)c2O)s1]

7-[5-(2-Dimethylaminomethyl-4-fluoro-benzyl)-thiazol-2-yl]-6-hydroxy-2-(4-methyl-piperazin-1-ylmethyl)-thiazolo[3,2-a]pyrimidin-5-one;

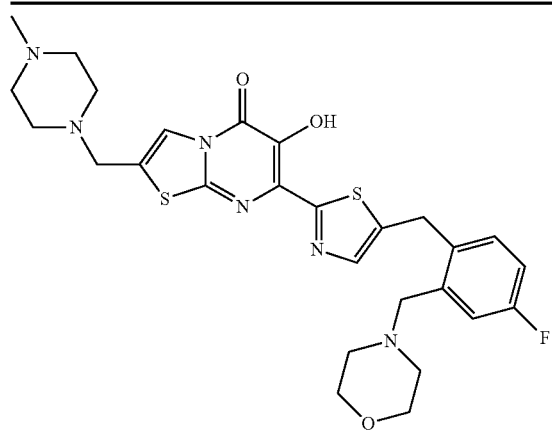

7-[5-(4-Fluoro-2-morpholin-4-ylmethyl-benzyl)-thiazol-2-yl]-6-hydroxy-2-(4-methyl-piperazin-1-ylmethyl)-thiazolo[3,2-a]pyrimidin-5-one;

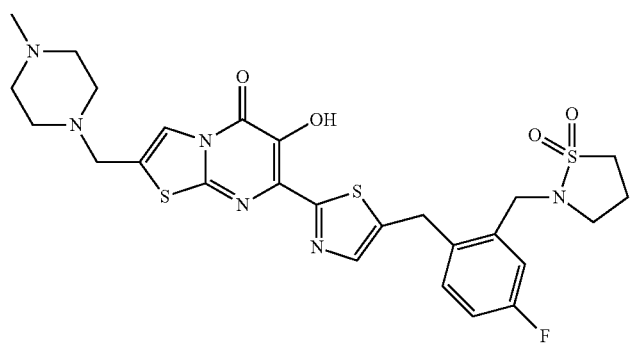 [SMILES: CN1CCN(Cc2cn3c(=O)c(O)c(-c4ncc(Cc5ccc(F)cc5CN5CCCS5(=O)=O)s4)nc3s2)CC1]

7-{5-[2-(1,1-Dioxo-isothiazolidin-2-ylmethyl)-4-fluoro-benzyl]-thiazol-2-yl}-6-hydroxy-2-(4-methyl-piperazin-1-ylmethyl)-thiazolo[3,2-a]pyrimidin-5-one; and

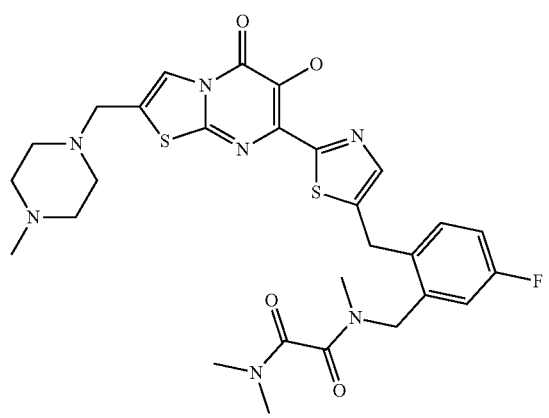 [SMILES: CN1CCN(Cc2cn3c(=O)c(O)c(-c4ncc(Cc5ccc(F)cc5CN(C)C(=O)C(=O)N(C)C)s4)nc3s2)CC1]

N-(5-Fluoro-2-{2-[6-hydroxy-2-(4-methyl-piperazin-1-ylmethyl)-5-oxo-5H-thiazolo[3,2-a]pyrimidin-7-yl]-thiazol-5-ylmethyl}-benzyl)-N,N',N'-trimethyl-oxalamide.

10. A method of treating a viral infection in a subject comprising administering to said subject an effective amount of a compound according to claim 1 or a pharmaceutically acceptable salt thereof, wherein the viral infection is a HIV or SIV infection.

11. The method according to claim 10 wherein the HIV or SIV infection comprises a viral strain resistant to integrase inhibitors.

12. The method according to claim 11 wherein the viral strain comprises HIV integrase enzyme containing the Q148H/G140S double mutation, N155H/E92Q double mutation, the F121Y/T124K double mutation or the Q148K/G140A/E138A triple mutation.

13. A pharmaceutical composition comprising a compound according to claim 1 and a pharmaceutically acceptable carrier, diluent or excipient.

14. The method according to claim 11, wherein the integrase inhibitors are selected from raltregavir or elvitegravir.

* * * * *